United States Patent
Skoda

(10) Patent No.: US 12,260,947 B2
(45) Date of Patent: Mar. 25, 2025

(54) SYSTEMS AND METHODS FOR MANAGING A MEDICAL SUPPLY CHAIN

(71) Applicant: Zorday IP, LLC, Mayfield Village, OH (US)

(72) Inventor: Brent M. Skoda, Mayfield Village, OH (US)

(*) Notice: Subject to any disclaimer, the term of this patent is extended or adjusted under 35 U.S.C. 154(b) by 0 days.

(21) Appl. No.: 18/110,858

(22) Filed: Feb. 16, 2023

(65) Prior Publication Data

US 2023/0197236 A1    Jun. 22, 2023

Related U.S. Application Data

(63) Continuation of application No. 16/994,919, filed on Aug. 17, 2020, now abandoned, which is a
(Continued)

(51) Int. Cl.
*G16H 20/13*    (2018.01)
*G16H 20/10*    (2018.01)
(Continued)

(52) U.S. Cl.
CPC ........... *G16H 20/13* (2018.01); *G16H 20/10* (2018.01); *G16H 40/20* (2018.01); *G16H 40/67* (2018.01)

(58) Field of Classification Search
None
See application file for complete search history.

(56) References Cited

U.S. PATENT DOCUMENTS 8,155,786 B2 *  4/2012  Vahlberg ............... G16H 40/67
                                                700/242
10,545,048 B2 *  1/2020  Pilkington ............... A61J 1/05
(Continued)

OTHER PUBLICATIONS

Petri Vuorimaa et al. 2012. Active life home: a portal-based home care platform. In Proceedings of the 5th International Conference on PErvasive Technologies Related to Assistive Environments (PETRA '12). Association for Computing Machinery, New York, NY, USA, Article 28, 1-8. (Year: 2012).*

(Continued)

*Primary Examiner* — Jonathan Ng
(74) *Attorney, Agent, or Firm* — Foley & Lardner LLP

(57) ABSTRACT

The present disclosure relates to systems and methods for managing a medical supply chain. According to one aspect, a remote medical management environment can include a medical management system intermediary to a plurality of patients and a plurality of medical care providers. The medical management system can communicate with medical dispensing devices configured to dispense medication to patients. Further, the medical management system can communicate with provider devices through which medical care providers can provide information regarding services provided to users or instructions associated with medication use. The medical management system can detect medication supply events based on information communicated by the medical dispensing devices and/or provider devices or based on information stored at the medical management system. Upon detecting a supply/refill event, the medical management system can initiate a supply refill process for supplying medication or medical device(s) to a patient.

20 Claims, 9 Drawing Sheets

Related U.S. Application Data continuation of application No. 16/258,530, filed on Jan. 25, 2019, now abandoned, which is a continuation of application No. 15/144,025, filed on May 2, 2016, now abandoned.

(60) Provisional application No. 62/155,847, filed on May 1, 2015.

(51) Int. Cl.
*G16H 40/20* (2018.01)
*G16H 40/67* (2018.01)

(56) References Cited

U.S. PATENT DOCUMENTS

| | | | |
|---|---|---|---|
| 2002/0032582 A1* | 3/2002 | Feeney, Jr. | G07F 17/0092 |
| | | | 700/231 |
| 2003/0036683 A1 | 2/2003 | Kehr et al. | |
| 2008/0059228 A1* | 3/2008 | Bossi | G16H 30/20 |
| | | | 705/2 |
| 2012/0035760 A1* | 2/2012 | Portney | G16H 20/13 |
| | | | 700/231 |
| 2012/0072231 A1* | 3/2012 | Mayer | G16H 20/10 |
| | | | 705/2 |
| 2012/0278531 A1 | 11/2012 | Horn | |
| 2014/0058560 A1* | 2/2014 | Kanagala | A61J 1/00 |
| | | | 700/240 |
| 2014/0058561 A1 | 2/2014 | Rothschild | |
| 2014/0303989 A1 | 10/2014 | Ferguson | |
| 2017/0017774 A1* | 1/2017 | Skoda | G16H 20/13 |
| 2017/0032102 A1* | 2/2017 | Skoda | G16H 20/13 |
| 2018/0078200 A1* | 3/2018 | Bowline | A61J 1/035 |
| 2019/0392936 A1* | 12/2019 | Arric | G16H 40/63 |

OTHER PUBLICATIONS

Non-Final Office Action on U.S. Appl. No. 15/144,025 Dtd Jul. 25, 2018.

Non-Final Office Action on U.S. Appl. No. 16/258,530 Dtd Feb. 18, 2020.

Non-Final Office Action on U.S. Appl. No. 16/994,919 Dtd Aug. 17, 2022.

* cited by examiner

SYSTEMS AND METHODS FOR MANAGING A MEDICAL SUPPLY CHAIN

RELATED APPLICATIONS

This patent application is a continuation of, and claims the benefit of and priority to U.S. patent application Ser. No. 16/994,919, titled "SYSTEMS AND METHODS FOR MANAGING A MEDICAL SUPPLY CHAIN," and filed Aug. 17, 2020, which is a continuation of, and claims the benefit of and priority to U.S. patent application Ser. No. 16/258,530, titled "SYSTEMS AND METHODS FOR MANAGING A MEDICAL SUPPLY CHAIN," and filed Jan. 25, 2019, which is a continuation of, and claims the benefit of and priority to U.S. patent application Ser. No. 15/144,025, titled "SYSTEMS AND METHODS FOR MANAGING A MEDICAL SUPPLY CHAIN," and filed May 2, 2016, which claims the benefit of and priority to U.S. Provisional Application No. 62/155,847, titled "SYSTEMS AND METHODS FOR MANAGING A MEDICAL SUPPLY CHAIN," and filed May 1, 2015, the contents all of which are hereby incorporated herein by reference in its entirety for all purposes.

FIELD OF THE DISCLOSURE

The present application relates generally to systems and methods for medical dispensing, management and monitoring, and more particularly, to methods and systems for managing a medical supply chain.

BACKGROUND

Patients in need of medication either have to visit pharmacies to pick up medication or have the medicines delivered to them. Oftentimes, doctors treating these patients are unable to gauge the efficacy of the medications they prescribe until the patient either returns to the clinic for follow up testing or goes to a laboratory for blood work.

SUMMARY

The present disclosure relates to systems and methods for managing a medical supply chain. According to one aspect, a remote medical management environment can include a medical management system intermediary to a plurality of patients and a plurality of medical care providers. The medical management system can communicate with medical dispensing devices configured to dispense medication to patients. Further, the medical management system can communicate with provider devices through which medical care providers can provide information regarding services provided to users or instructions associated with medication use. The medical management system can detect medication supply events based on information communicated by the medical dispensing devices and/or provider devices or based on information stored at the medical management system. Upon detecting a supply/refill event, the medical management system can initiate a supply refill process for supplying medication or medical device(s) to a patient.

In some implementations, the medical management system can be configured to determine supply/refill events based on a remotely monitored medication dispensing rate. The medical management system can estimate or calculate the medication dispensing rate based on reported dispensing events. Using the medication dispensing rate, the medical management system can determine an expected supply/refill date. In some implementations, the medical management system can detect a supply/refill event based on communications from provider devices including explicit requests for supply/refill, indication of a new prescription, or reminder of an approaching refill date.

According to at least one aspect, the medial management system can execute a supply/refill process based on patient location. The medical management system can be configured to determine a patient location, for instance, based on GPS data provided by communication device or medical dispensing device of the patient, information provided by a provider and/or other communications with patient (e.g., via email, SMS, chat or voice communication). The medical management system can be configured to determine a provider store or facility of providing medication the patient based on the patient's location. Other factors in determining a pharmacy provider can include medication price by each provider, user preferences, medical insurance requirements, medication type and/or medication availability at each potential provider store. In some implementations, the medical management system can be configured to obtain patient approval/confirmation regarding selected provider(s). The medical management system can send a supply/refill request to a selected provider and inform patient.

The medical management system can include a processor and a memory including instructions configured to cause the medical management system to allow a medical care provider to remotely manage and administer medications to one or more patients. The medical management system includes a patient database, a provider database, a medical manager and a prescription manager. The medical management system can include one or more communication modules through which the medical management system can communicate with patient devices and provider devices. The medical management system can include an inventory manager for full or partial remote management of a medical provider inventory. The medical management system can include a patient location manager for managing or monitoring patient location over time.

According to at least one aspect, the medical management system can be configured to collect patient location data based on communications with patient devices, provider devices or a combination thereof. Patient devices, such as medical dispensing devices, mobile devices, wearable devices, etc., can be configured to report respective location when reporting medical measurements, sensor measurement, dispensing events, etc. In some implementations, patient devices can be configured to communicate respective location(s) to the medical management system periodically or upon request from the medical management system. The patient location manager can be configured to apply location determination policy to determine locations of interest.

According to at least one aspect, the inventory manager can be configured to manage medical provider inventory with regard to all medical product or specific items. The medical management system can be configured to obtain periodic or transaction-based updates from a point of sale (POS) terminal of the medical provider indicative of amount of medication (or medical devices) sold. The medical management system can also have access (or receive indications) of medication replenishment events at provider stores. The medical management system can use maintained provider inventory information when selecting a provider store for medication supply/refill to a patient. Remote inventory management can be offered as a service for medical providers.

According to at least one aspect, the medical management system can be configured to provide a variety of service packages for medical providers. Each service package can include one or more services provided by the medical management system, such as GPS and location based services, radio-frequency identification of medication and medical devices, medication dispensing monitoring, full and partial remote inventory management, access to statistical data generated by the medical management system, bidding for refill/supply events, advertisement to patients and other users, etc. In some implementations, service packages can be provided through a respective computer, mobile or web application/platform instances. The medical management system can offer different levels of services that involve different features. A first level may provide inventory management, a second level may provide inventory management as well as patient coordination management, and a third level may provide inventory management, patient coordination management and automatic location based medication delivery management.

The patient device, otherwise referred to as a medical dispensing device can be configured to allow a medical care provider, for example, a doctor, the ability to remotely monitor, regulate and manipulate medication administration to a patient associated with the patient device. Through the medical dispensing device, the medical care provider can adjust either the dosage of medications or the time at which the medication is administered. In some implementations, the medical care provider may receive feedback through the medical dispensing device or other medical device monitoring the patient and adjust the dosage or time at which to administer medication based on the received feedback. The medical dispensing device can be equipped with a communications module that is configured to communicate with the medical management system through which the medical care provider can remotely communicate with the medical dispensing device. The communications module can include both hardware and software components that allow the medical dispensing device to receive and transmit instructions and information. In some implementations, the communications module can be configured to provide wireless communications, for example, BLUETOOTH, WiFi, cellular communications, near-field communication (NFC), among others. In some implementations, the communications module can be configured to communicate with another device, such as a smartphone, tablet, or other device that allows the medical dispensing device to receive and execute instructions received from the medical care provider. The medical dispensing device can include one or more electronic actuators that can be configured or programmed to control the amount of medication dispensed from the medical dispensing device.

In some implementations, the medical dispensing device is programmable and capable of maintaining activity logs. The activity logs can identify a date and time at which medication was dispensed, a dosage of medication dispensed as well as any other physiological measurements, for example, temperature, pulse, heart rate, blood pressure, sugar levels, among others, taken around the time the medication was dispensed. In addition to medication dispensing related activity, the activity logs can identify when a medical care provider communicated with the medical dispensing device. In some implementations, the activity logs can include information related to dosage changes as well as changes in the time at which medication is to be administered.

The medical dispensing device can also include sensors measuring a quantity of medication remaining in the medical dispensing device. In some implementations, the medical dispensing device an determine an amount of medication remaining in the medical dispensing device based on the amount of medication included in a medicine cartridge and an amount of medication already dispensed since the medicine cartridge was first inserted. The medical dispensing device can be configured to communicate medicine quantity levels such that refills can be ordered before the medicine cartridge is completely empty.

The medical dispensing device can be tamper proof. This is to prevent medication abuse and fraud. In some implementations, the medical dispensing device can include an alert system that triggers an alert upon determining that the medical dispensing device has been tampered or an attempt to tamper the medical dispensing device was made. In some implementations, the medical dispensing device can include one or more security modules. The security modules can include hardware and software to ensure that the medication is dispensed to an authorized user or patient. In some implementations, the medical dispensing device can include a user recognition or identification system. In some implementations, the medical dispensing device can include a fingerprint reader, an iris scanner, or any other biometric scanner to confirm the identity of the user. In some implementations, the medical dispensing device can be password protected. In some implementations the medical dispensing device can only be actuated via a second device, such as a smartphone or tablet, registered with the medical management system.

In some implementations, the medical dispensing device can include a temperature control module to control the temperature of medication within the medical dispensing device. In this way, if the medicine in the medical dispensing device is to be maintained at a particular temperature, and the medical dispensing device is in a location that has an ambient temperature much higher than the temperature at which to maintain the medicine, the medical dispensing device can provide cooling to the medication. Conversely, the medical dispensing device can provide heating to medications that are supposed to be stored or maintained at temperatures higher than the ambient temperature at which the medical dispensing device is located.

In some implementations, the medical dispensing device can be a programmable, remotely controlled prescription drug bottle. The medical dispensing device may include Bluetooth, RFID, GPS, a battery, a controller, a cellular chip, etc. The medical dispensing device could dispense pills, liquid, powder, any vaporizable substance, collectively, respectively, and independently. The medical dispensing device can be configured to provide the ability to remotely regulate, monitor, control and/or verify dosage. In this way, a medical care provider can regulate or control the number of pills dispensed, the time at which they are dispensed and the location at which they can be dispensed, among others. For instance, if the pills can only be dispensed within a particular geographic location identifiable via cellular triangulation techniques, IP addressing, or GPS coordinates, the risk of drug abuse, theft, resale, and redistribution can be minimized. In some implementations, the medical dispensing device can be configured to only dispense medications when it is within a few feet from a stationary object, such as a RFID scanner or Bluetooth source that may be tied to a particular location.

In some implementations, the medical dispensing device may be configured to communicate with a mobile device of the patient to verify the identity of a person accessing or requesting access to the medical dispensing device. For instance, the medical dispensing device may only dispense medication in response to receiving a communication or signal from a paired mobile device that can generate the communication or signal upon verifying the identity of the patient. In some implementations, the mobile device can verify the identity of the patient through facial recognition, fingerprint scanning, passwords, or other security measures that can be received, identified or otherwise incorporated via the mobile device. In this way, there is no need for the medical dispensing device to be designed with an integrated fingerprint scanner, camera to detect facial recognition, or keypad to receive a password from the patient, thereby reducing manufacturing costs of the medical dispensing device.

In some implementations, the location of the medical dispensing device or the mobile device with which the medical dispensing device can communicate may be monitored. In some implementations, the medical dispensing device can restrict the dispensing of medications based on one or more predetermined locations. In some implementations, one or more location based policies can be established to ensure additional security. For instance, the medical dispensing device may be configured to only dispense the medicine at predetermined locations, for example, a patient's home, a patient's work location, a nursing home, a hospital or other medical care provider's address, among others. In this way, if the device is stolen or otherwise provided to an unauthorized user, the unauthorized user may be unable to receive medication from the medical dispensing device at locations different from the predetermined locations. In addition, the medical dispensing device may only transmit or receive data from the medical management system at the predetermined locations to reduce security breaches.

In some implementations, the medical dispensing device can operate using batteries. In some implementations, the batteries may be rechargeable or disposable. In some implementations in which the batteries are rechargeable, the batteries may be charged via a USB cable, via a power supply channel, or via wireless induction. In some implementations, to implement wireless induction, the medical dispensing device can be incorporated with a wireless charging coil, for example, a wireless charging coil supplied by DIGIKEY and manufactured by Wurth Electronics, Inc. In some implementations, the wireless charging coil can be Part Number 76030811, manufactured by Wurth Electronics, Inc. The shape, size and position of the one or more wireless charging coils can be designed to fit within the medical dispensing device.

DETAILED DESCRIPTION

For purposes of reading the description of the various embodiments below, the following descriptions of the sections of the specification and their respective contents may be helpful:

Section A describes a network environment and computing environment which may be useful for practicing embodiments described herein.

Section B describes embodiments of systems and methods for medical dispensing, management and monitoring.

Section C describes embodiments of systems and methods of remote medication management and monitoring.

Section D describes embodiments of systems and methods for managing a supply chain for providing patients with medication.

A. Computing and Network Environment

Figure 1A:
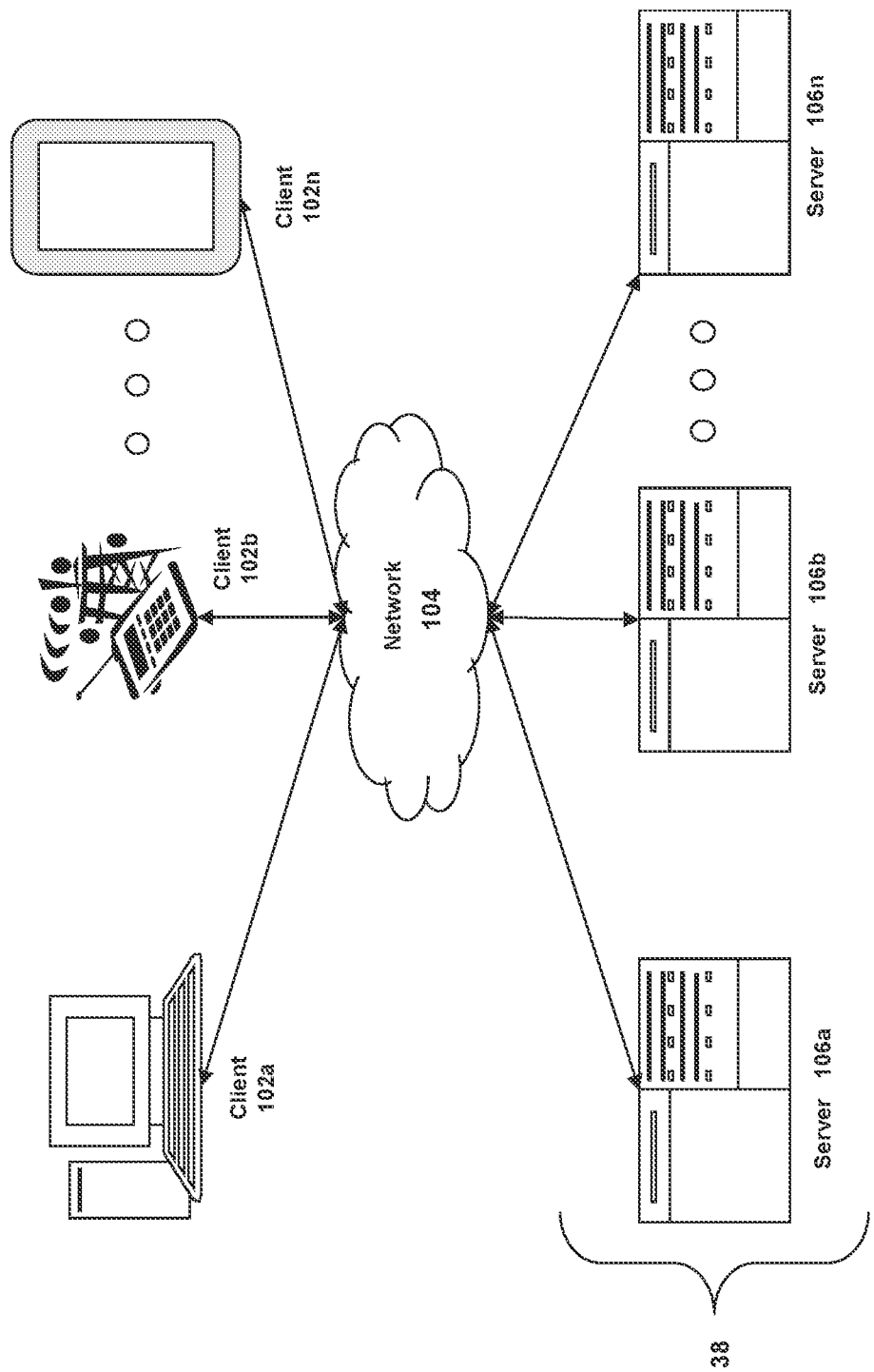
FIG. 1A is a block diagram depicting an embodiment of a network environment comprising local devices in communication with remote devices.

In addition to discussing specific embodiments of the present solution, it may be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 102a-102n (also generally referred to as local machine(s) 102, client(s) 102, client nodes) 102, client machine(s) 102, client computer(s) 102, client device(s) 102, endpoint(s) 102, or endpoint node(s) 102) in communication with one or more servers 106a-106n (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102a-102n.

Although FIG. 1A shows a network 104 between the clients 102 and the servers 106, the clients 102 and the servers 106 may be on the same network 104. In some embodiments, there are multiple networks 104 between the clients 102 and the servers 106. In one of these embodiments, a network 104' (not shown) may be a private network and a network 104 may be a public network. In another of these embodiments, a network 104 may be a private network and a network 104' a public network. In still another of these embodiments, networks 104 and 104' may both be private networks.

The network 104 may be connected via wired or wireless links. Wired links may include Digital Subscriber Line (DSL), coaxial cable lines, or optical fiber lines. The wireless links may include BLUETOOTH, Wi-Fi, Worldwide Interoperability for Microwave Access (WiMAX), an infrared channel or satellite band. The wireless links may also include any cellular network standards used to communicate among mobile devices, including standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 1G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

The network 104 may be any type and/or form of network. The geographical scope of the network 104 may vary widely and the network 104 can be a body area network (BAN), a personal area network (PAN), a local-area network (LAN), e.g. Intranet, a metropolitan area network (MAN), a wide area network (WAN), or the Internet. The topology of the network 104 may be of any form and may include, e.g., any of the following: point-to-point, bus, star, ring, mesh, or tree. The network 104 may be an overlay network which is virtual and sits on top of one or more layers of other networks 104'. The network 104 may be of any such network topology as known to those ordinarily skilled in the art capable of supporting the operations described herein. The network 104 may utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite may include application layer, transport layer, internet layer (including, e.g., IPv6), or the link layer. The network 104 may be a type of a broadcast network, a telecommunications network, a data communication network, or a computer network.

In some embodiments, the system may include multiple, logically-grouped servers 106. In one of these embodiments, the logical group of servers may be referred to as a server farm 38 or a machine farm 38. In another of these embodiments, the servers 106 may be geographically dispersed. In other embodiments, a machine farm 38 may be administered as a single entity. In still other embodiments, the machine farm 38 includes a plurality of machine farms 38. The servers 106 within each machine farm 38 can be heterogeneous—one or more of the servers 106 or machines 106 can operate according to one type of operating system platform (e.g., WINDOWS NT, manufactured by Microsoft Corp. of Redmond, Washington), while one or more of the other servers 106 can operate on according to another type of operating system platform (e.g., Unix, Linux, or Mac OS X).

In one embodiment, servers 106 in the machine farm 38 may be stored in high-density rack systems, along with associated storage systems, and located in an enterprise data center. In this embodiment, consolidating the servers 106 in this way may improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 may be interconnected using a wide-area network (WAN) connection or a metropolitan-area network (MAN) connection. For example, a machine farm 38 may include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 may include one or more servers 106 operating according to a type of operating system, while one or more other servers 106 execute one or more types of hypervisors rather than operating systems. In these embodiments, hypervisors may be used to emulate virtual hardware, partition physical hardware, virtualize physical hardware, and execute virtual machines that provide access to computing environments, allowing multiple operating systems to run concurrently on a host computer. Native hypervisors may run directly on the host computer. Hypervisors may include VMware ESX/ESXi, manufactured by VMWare, Inc., of Palo Alto, California; the Xen hypervisor, an open source product whose development is overseen by Citrix Systems, Inc.; the HYPER-V hypervisors provided by Microsoft or others. Hosted hypervisors may run within an operating system on a second software level. Examples of hosted hypervisors may include VMware Workstation and VIRTUALBOX.

Management of the machine farm 38 may be de-centralized. For example, one or more servers 106 may comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 may communicate with a persistent store and, in some embodiments, with a dynamic store.

Server 106 may be a file server, application server, web server, proxy server, appliance, network appliance, gateway, gateway server, virtualization server, deployment server, SSL VPN server, or firewall. In one embodiment, the server 106 may be referred to as a remote machine or a node. In another embodiment, a plurality of nodes 290 may be in the path between any two communicating servers.

Figure 1B:
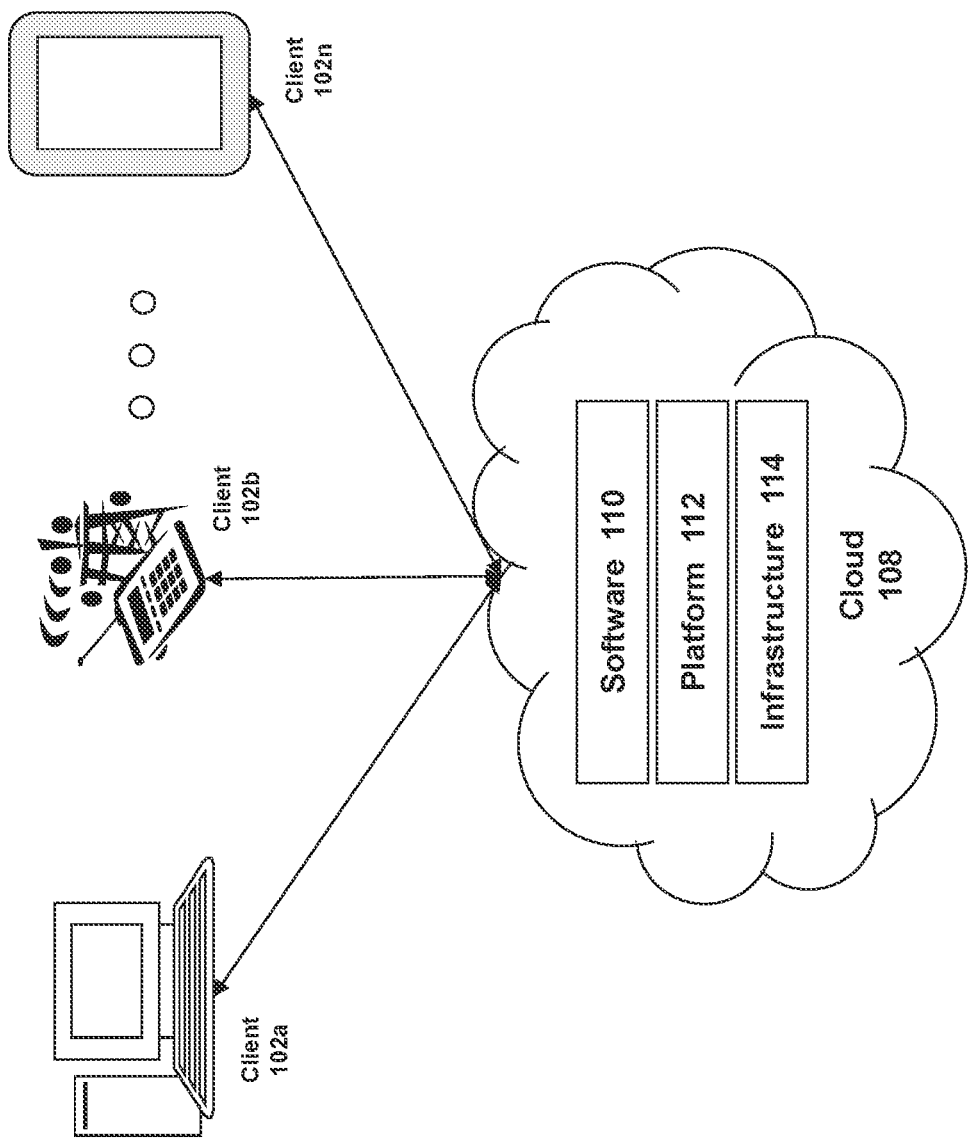
FIGS. 1B-1D are block diagrams depicting embodiments of computers useful in connection with the methods and systems described herein.

Referring to FIG. 1B, a cloud computing environment is depicted. A cloud computing environment may provide client 102 with one or more resources provided by a network environment. The cloud computing environment may include one or more clients 102a-102n, in communication with the cloud 108 over one or more networks 104. Clients 102 may include, e.g., thick clients, thin clients, and zero clients. A thick client may provide at least some functionality even when disconnected from the cloud 108 or servers 106. A thin client or a zero client may depend on the connection to the cloud 108 or server 106 to provide functionality. A zero client may depend on the cloud 108 or other networks 104 or servers 106 to retrieve operating system data for the client device. The cloud 108 may include back end platforms, e.g., servers 106, storage, server farms or data centers.

The cloud 108 may be public, private, or hybrid. Public clouds may include public servers 106 that are maintained by third parties to the clients 102 or the owners of the clients. The servers 106 may be located off-site in remote geographical locations as disclosed above or otherwise. Public clouds may be connected to the servers 106 over a public network. Private clouds may include private servers 106 that are physically maintained by clients 102 or owners of clients. Private clouds may be connected to the servers 106 over a private network 104. Hybrid clouds 108 may include both the private and public networks 104 and servers 106.

The cloud 108 may also include a cloud based delivery, e.g. Software as a Service (SaaS) 110. Platform as a Service (PaaS) 112, and Infrastructure as a Service (IaaS) 114. IaaS may refer to a user renting the use of infrastructure resources that are needed during a specified time period. IaaS providers may offer storage, networking, servers or virtualization resources from large pools, allowing the users to quickly scale up by accessing more resources as needed. Examples of IaaS include AMAZON WEB SERVICES provided by Amazon.com, Inc., of Seattle, Washington, RACKSPACE CLOUD provided by Rackspace US, Inc., of San Antonio, Texas, Google Compute Engine provided by Google Inc. of Mountain View, California, or RIGHTSCALE provided by RightScale, Inc., of Santa Barbara, California. PaaS providers may offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Washington, Google App Engine provided by Google Inc., and HEROKU provided by Heroku, Inc. of San Francisco, California. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc., SALESFORCE provided by Salesforce.com Inc. of San Francisco, California, or OFFICE 365 provided by Microsoft Corporation. Examples of SaaS may also include data storage providers, e.g. DROPBOX provided by Dropbox, Inc. of San Francisco, California, Microsoft SKYDRIVE provided by Microsoft Corporation, Google Drive provided by Google Inc., or Apple ICLOUD provided by Apple Inc. of Cupertino, California.

Clients 102 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP, and may use Representational State Transfer (REST) protocol or Simple Object Access Protocol (SOAP). Clients 102 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 102 may access SaaS resources through the use of web-based user interfaces, provided by a web browser (e.g. GOOGLE CHROME, Microsoft INTERNET EXPLORER, or Mozilla Firefox provided by Mozilla Foundation of Mountain View, California). Clients 102 may also access SaaS resources through smartphone or tablet applications, including, for example, Salesforce Sales Cloud, or Google Drive app. Clients 102 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as, e.g., Advanced. Encryption Standard (AES). Data resources may be sent over Transport Layer Security (TLS) or Secure Sockets Layer (SSL).

Figure 1C:
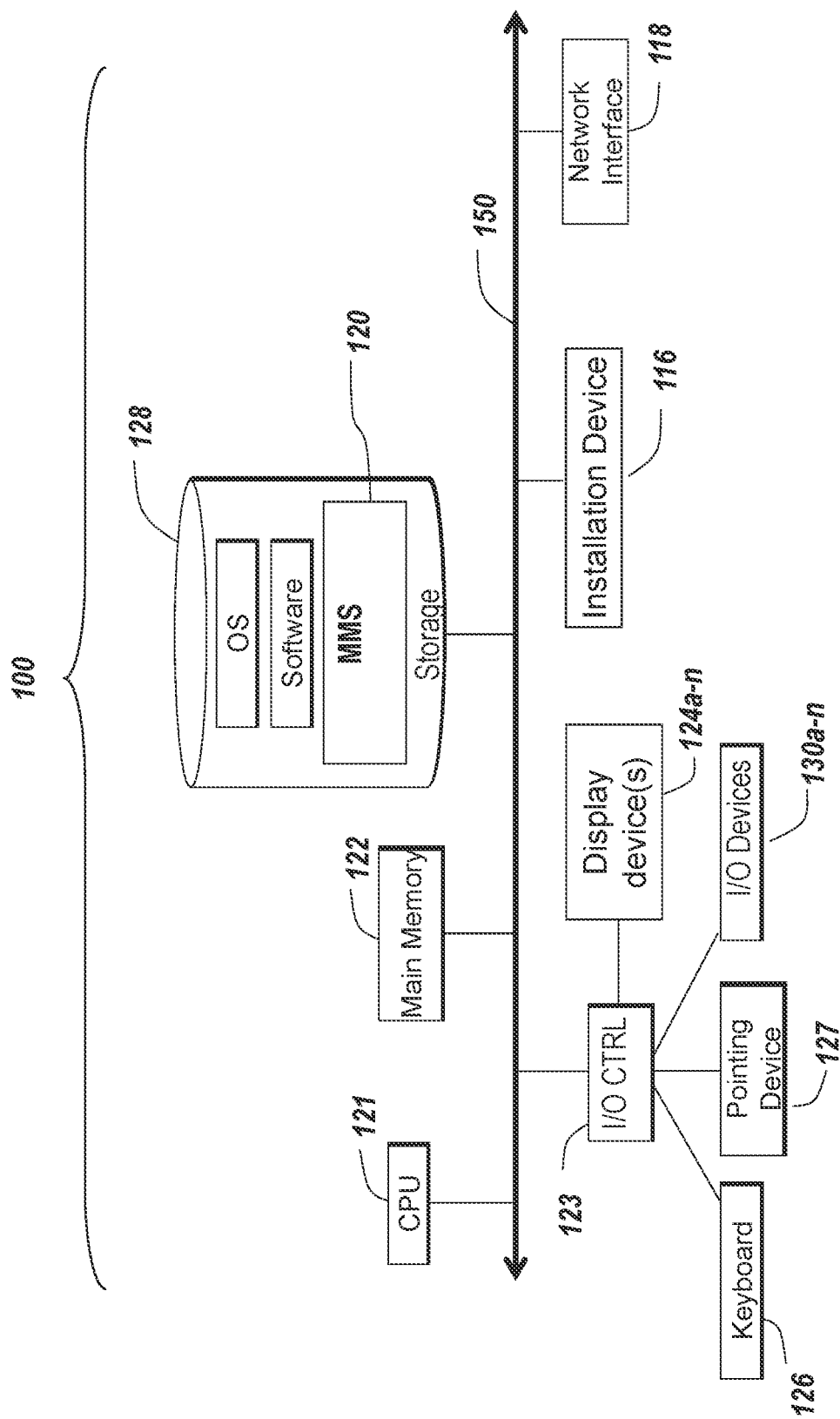
Figure 1D:
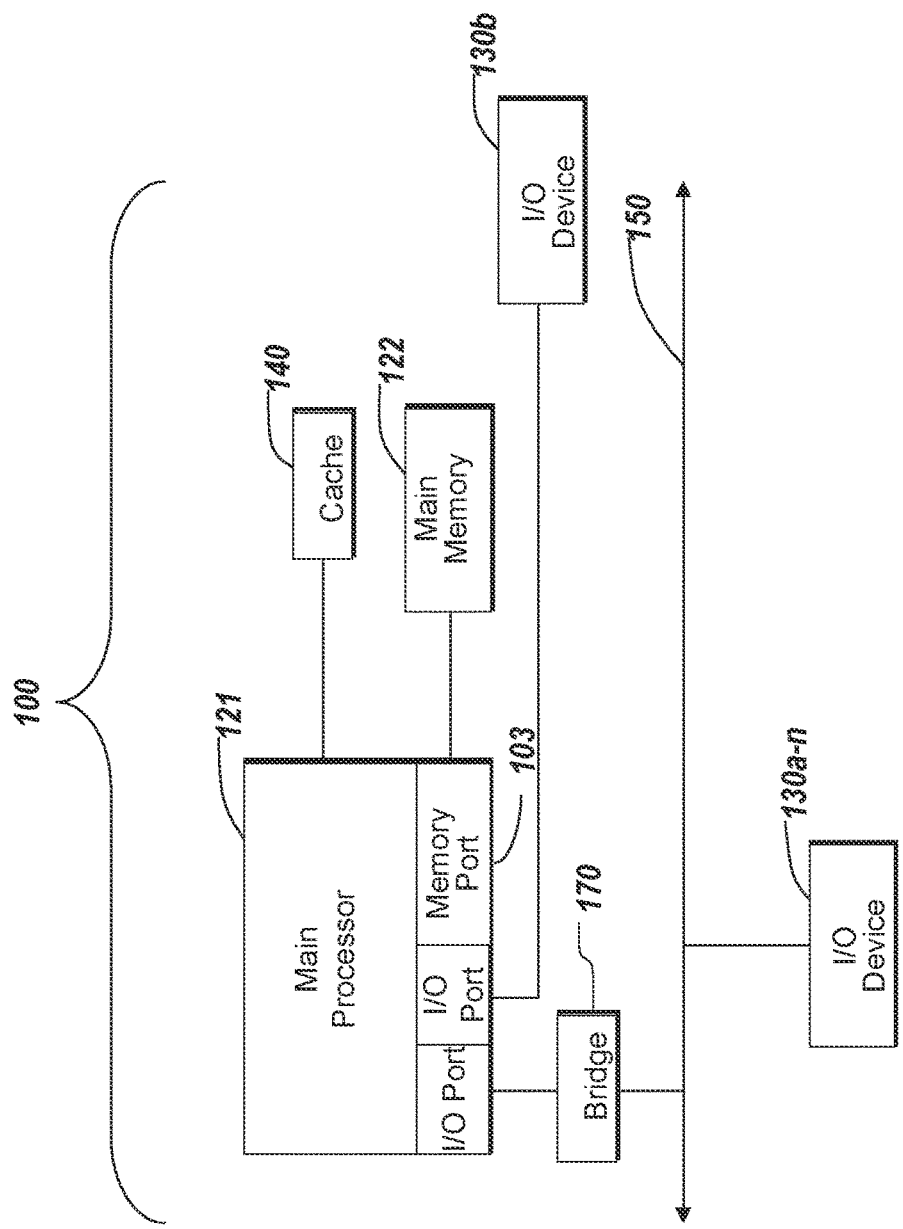

The client 102 and server 106 may be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 may include a storage device 128, an installation device 116, a network interface 118, an I/O controller 123, display devices 124a-124n, a keyboard 126 and a pointing device 127, e.g. a mouse. The storage device 128 may include, without limitation, an operating system, software, and a software of a medical management system (MMS) 120. As shown in FIG. 1D, each computing device 100 may also include additional optional elements, e.g. a memory port 103, a bridge 170, one or more input/output devices 130a-130n (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, California; those manufactured by Motorola Corporation of Schaumburg, Illinois; the ARM processor and TEGRA system on a chip (SoC) manufactured by Nvidia of Santa Clara, California; the POWER7 processor, those manufactured by international Business Machines of White Plains, New York; or those manufactured by Advanced Micro Devices of Sunnyvale, California. The computing device 100 may be based on any of these processors, or any other processor capable of operating as described herein. The central processing unit 121 may utilize instruction level parallelism, thread level parallelism, different levels of cache, and multi-core processors. A multi-core processor may include two or more processing units on a single computing component. Examples of a multi-core processors include the AMD PHENOM IIX2, INTEL CORE i5 and INTEL CORE i7.

Main memory unit 122 may include one or more memory chips capable of storing data and allowing any storage location to be directly accessed by the microprocessor 121. Main memory unit 122 may be volatile and faster than storage 128 memory. Main memory units 122 may be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 may be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 may be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 may be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various 110 devices 130 via a local system bus 150. Various buses may be used to connect the central processing unit 121 to any of the I/O devices 130, including a PCI bus, a PCI-X bus, or a PCI-Express bus, or a NuBus. For embodiments in which the I/O device is a video display 124, the processor 121 may use an Advanced Graphics Port (AGP) to communicate with the display 124 or the I/O controller 123 for the display 124. FIG. 1D depicts an embodiment of a computer 100 in which the main processor 121 communicates directly with I/O device 130b or other processors 121' via HYPERTRANSPORT, RAPIDIO, or INFINIBAND communications technology. FIG. 1D also depicts an embodiment in which local busses and direct communication are mixed: the processor 121 communicates with I/O device 130a using a local interconnect bus while communicating with I/O device 130b directly.

A wide variety of I/O devices 130a-130n may be present in the computing device 100. Input devices may include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices may include video displays, graphical displays, speakers, headphones, inkjet printers, laser printers, and 3D printers.

Devices 130a-130n may include a combination of multiple input or output devices, including, e.g., Microsoft KINECT, Nintendo Wiimote for the WII, Nintendo WII U GAMEPAD, or Apple IPHONE. Some devices 130a-130n allow gesture recognition inputs through combining some of the inputs and outputs. Some devices 130a-130n provides for facial recognition which may be utilized as an input for different purposes including authentication and other commands. Some devices 130a-130n provides for voice recognition and inputs, including, e.g., Microsoft KINECT, SIRI for IPHONE by Apple, Google Now or Google Voice Search.

Additional devices 130a-130n have both input and output capabilities, including, e.g., haptic feedback devices, touchscreen displays, or multi-touch displays. Touchscreen, multi-touch displays, touchpads, touch mice, or other touch sensing devices may use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices may allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, may have larger surfaces, such as on a table-top or on a wall, and may also interact with other electronic devices. Some 110 devices 130a-130n, display devices 124a-124n or group of devices may be augment reality devices. The I/O devices may be controlled by an I/O controller 123 as shown in FIG. 1C. The I/O controller may control one or more I/O devices, such as, e.g., a keyboard 126 and a pointing device 127, e.g., a mouse or optical pen. Furthermore, an I/O device may also provide storage and/or an installation medium 116 for the computing device 100. In still other embodiments, the computing device 100 may provide USB connections (not shown) to receive handheld USB storage devices. In further embodiments, an I/O device 130 may be a bridge between the system bus 150 and an external communication bus, e.g. a USB bus, a SCSI bus, a FireWire bus, an Ethernet bus, a Gigabit Ethernet bus, a Fibre Channel bus, or a Thunderbolt bus.

In some embodiments, display devices 124a-124n may be connected to 110 controller 123. Display devices may include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays may use, e.g. stereoscopy, polarization filters, active shutters, or autostereoscopy. Display devices 124a-124n may also be a head-mounted display (HMD). In some embodiments, display devices 124a-124n or the corresponding I/O controllers 123 may be controlled through or have hardware support for OPENGL or DIRECTX API or other graphics libraries.

In some embodiments, the computing device 100 may include or connect to multiple display devices 124a-124n, which each may be of the same or different type and/or form. As such, any of the I/O devices 130a-130n and/or the I/O controller 123 may include any type and/or form of suitable hardware, software, or combination of hardware and software to support, enable or provide for the connection and use of multiple display devices 124a-124n by the computing device 100. For example, the computing device 100 may include any type and/or form of video adapter, video card, driver, and/or library to interface, communicate, connect or otherwise use the display devices 124a-124n. In one embodiment, a video adapter may include multiple connectors to interface to multiple display devices 124a-124n. In other embodiments, the computing device 100 may include multiple video adapters, with each video adapter connected to one or more of the display devices 124a-124n. In some embodiments, any portion of the operating system of the computing device 100 may be configured for using multiple displays 124a-124n. In other embodiments, one or more of the display devices 124a-124n may be provided by one or more other computing devices 100a or 100b connected to the computing device 100, via the network 104. In some embodiments software may be designed and constructed to use another computer's display device as a second display device 124a for the computing device 100. For example, in one embodiment, an Apple iPad may connect to a computing device 100 and use the display of the device 100 as an additional display screen that may be used as an extended desktop. One ordinarily skilled in the art will recognize and appreciate the various ways and embodiments that a computing device 100 may be configured to have multiple display devices 124a-124n.

Referring again to FIG. 1C, the computing device 100 may comprise a storage device 128 (e.g. one or more hard disk drives or redundant arrays of independent disks) for storing an operating system or other related software, and for storing application software programs such as any program related to the software for the medical monitoring system 120. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices may include multiple volatile and non-volatile memories, including, e.g., solid state hybrid drives that combine hard disks with solid state cache. Some storage device 128 may be non-volatile, mutable, or read-only. Some storage device 128 may be internal and connect to the computing device 100 via a bus 150. Some storage device 128 may be external and connect to the computing device 100 via a I/O device 130 that provides an external bus. Some storage device 128 may connect to the computing device 100 via the network interface 118 over a network 104, including, e.g., the Remote Disk for MACBOOK AIR by Apple. Some client devices 100 may not require a non-volatile storage device 128 and may be thin clients or zero clients 102. Some storage device 128 may also be used as an installation device 116, and may be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 may also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform may facilitate installation of software on a client device 102. An application distribution platform may include a repository of applications on a server 106 or a cloud 108, which the clients 102a-102n may access over a network 104. An application distribution platform may include application developed and provided by various developers. A user of a client device 102 may select, purchase and/or download an application via the application distribution platform.

Furthermore, the computing device 100 may include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 118 may comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C may operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. of London, United Kingom; or Unix or other Unix-like derivative operating systems; and Android, designed by Google, of Mountain View, California, among others. Some operating systems, including, e.g., the CHROME OS by Google, may be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 may have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 may comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Washington.

In some embodiments, the computing device 100 is a digital audio player such as the Apple IPOD, IPOD Touch, and IPOD NANO lines of devices, manufactured by Apple Computer of Cupertino, California. Some digital audio players may have other functionality, including, e.g., a gaming system or any functionality made available by an application from a digital application distribution platform. For example, the IPOD Touch may access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Washington. In other embodiments, the computing device 100 is a eBook reader, e.g. the KINDLE family of devices by Amazon.com, or NOOK family of devices by Barnes & Noble, Inc. of New York City, New York.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 is monitored, generally as part of network management. In one of these embodiments, the status of a machine may include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information may be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Systems and Methods for Medical Dispensing, Management and Monitoring

The present disclosure relates to systems and methods for medical dispensing, management and monitoring. According to one aspect, a remote medical management environment can include a medical management system intermediary to a plurality of patients and a plurality of medical care providers. The medical management system can communicate with medical dispensing devices configured to dispense medication to patients. Further, the medical management system can communicate with provider devices through which medical care providers can access medicine related information of patients and provide instructions, which can administer treatment protocols to patients of the medical dispensing devices. The remote medical management environment can allow medical care providers, such as doctors, the ability to remotely manage and administer medications to patients, while at the same time, avoid medicinal drug abuse by patients.

Figure 2:
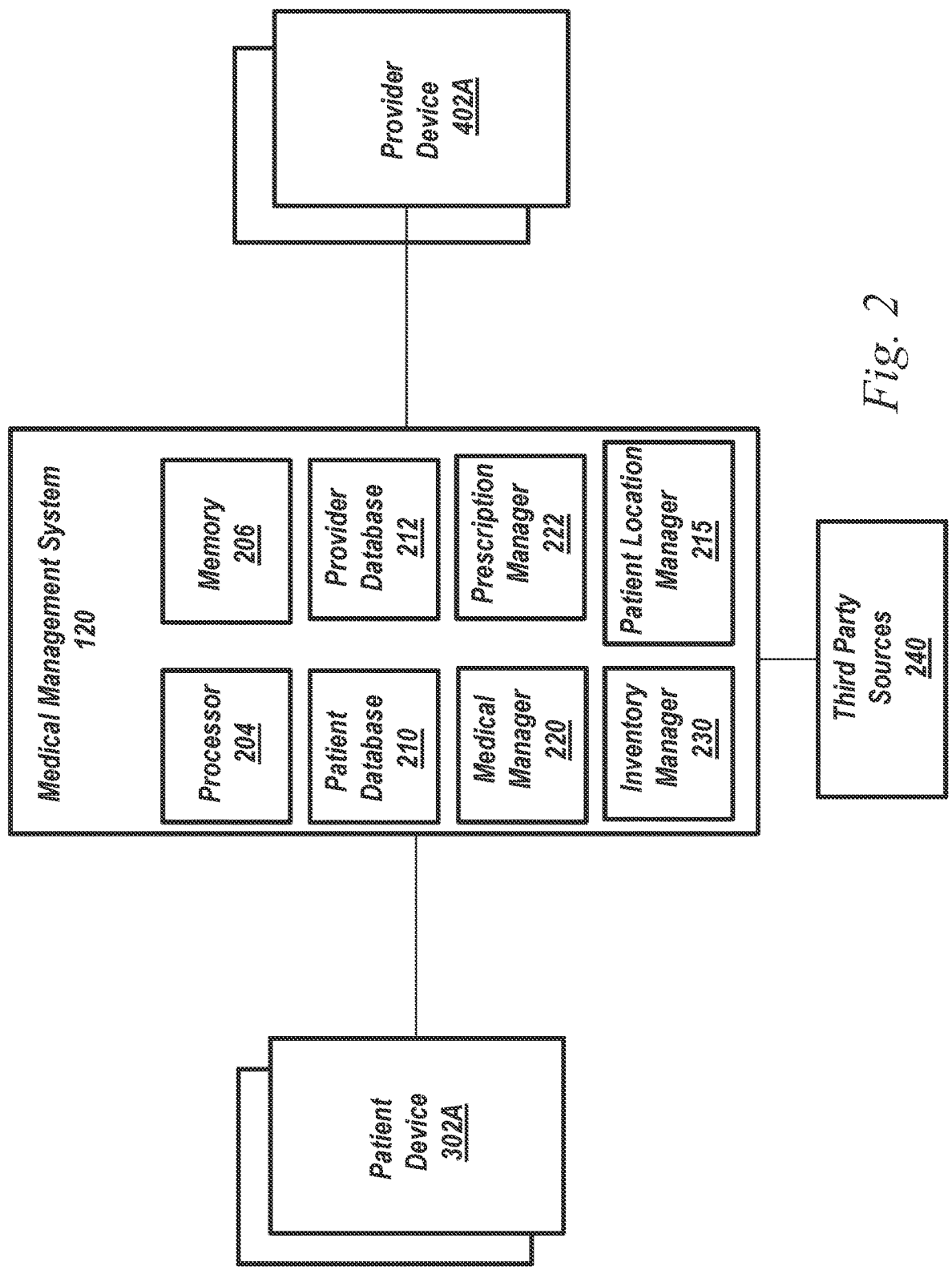
FIG. 2 is a block diagram depicting a medical management environment including a medical management system intermediary to a plurality of provider devices and patient devices.

FIG. 2 is a block diagram depicting a medical management environment including a medical management system 120 intermediary to a plurality of patient devices 302A-302N and provider devices 402A-402N. The medical management system 120 can communicate with the plurality of patient devices 302 via one or more networks. Similarly, the medical management system 120 can also communicate with the plurality of provider devices 302 via one or more networks. The medical management system 120 can include one or more processors 204, memory 206, one or more patient databases 210, one or more provider databases 212, a medical manager 220 and a prescription manager 222. The medical management system 120 can also communicate with one or more third-party data sources 240, for example, weather databases, location databases, pharmaceutical drug databases, pharmacy databases, among others.

The patient database 210 can include one or more tables storing information related to one or more patients and their corresponding patient devices. The patient database can include information relating to one or more patients registered with the medical management system 120. In some implementations, the patient database can store, for each patient, one or more of the patient's name, the patient's identifier unique to the patient, the patient's date of birth, a phone number of the patient, home and work addresses of the patient, information related to the patient's medical records, for example, medical history, medical diagnosis, medical treatments, among others. In addition, the database can include prescription information for the patient, dosage information, allergies of the patient, medical care provider's name, pharmacy name, address and phone number, prescription information, health insurance information, among others. The patient database can also include a patient device identifier unique to the patient device and associated with the patient. The patient database can be maintained by the medical management system 120. In some implementations, the medical management system 120 can periodically update the patient database. In some implementations, each time the medical management system 120 receives information from a provider device 402 of a medical care provider or a patient device 302 of a patient, the medical management system 120 can identify the patient to which the information corresponds and update the patient database 210 to update an entry of the patient to include the received information.

The provider database 212 can include one or more tables storing information related to one or more medical care providers. The patient database can include information relating to one or more medical care providers registered with the medical management system 120 to manage and monitor patients and their medications via the medical management system 120. In some implementations, the provider database 212 can store, for each provider, one or more of the provider's name, the provider's identifier unique to the provider, the provider's date of birth, a phone number of the provider, home and work addresses of the provider, information related to the provider's medical licensing information, among others. In addition, the provider database 212 can include a list of patients the medical provider is authorized to treat via the medical management system 120. The provider database 212 can be maintained by the medical management system 120. In some implementations, the medical management system 120 can periodically update the provider database 212. In some implementations, each time the medical management system 120 receives information from a provider device 402 of a medical care provider or a patient device 302 of a patient, the medical management system 120 can identify the medical care provider to which the information corresponds and update the provider database 212 to update an entry of the provider to include the received information.

The medical manager 220 can include hardware, software or a combination of hardware and software. The medical manager 220 can be a script, program, file, or other software construct, which when executed by the processor 204, can be configured to communicate with one or more patient devices 302 and one or more provider devices 402. The medical manager 220 can be configured to allow a provider device 402 to remotely dispense, manage and monitor medications provided to a patient via a patient device 302.

The medical manager 220 can be configured to establish communications with the provider device 402. In some implementations, the medical manager 220 can initiate a request to communicate with the provider device 402. In some implementations, the medical manager 220 can initiate a request to communicate with the provider device 402 in response to a triggering event, for example, receiving a communication request from a patient or a patient device, determining that a patient device is running low on a prescription medication, identifying that a patient of the provider needs the provider's attention, among others. In some implementations, the medical manager 220 can receive a request from the provider device to establish a communication link with the medical manager 220. The provider may submit a request via the provider device to access a provider dashboard through which the provider can monitor the status of patients and the associated patient devices 302.

The medical manager 220 can be configured to provide a user interface to the provider device 402. In some implementations, the medical manager 220 can be configured to receive a request from the provider device 402 to access information related to a patient. The request can include identifying information of the medical care provider. The medical manager 220 can perform a lookup in the provider database 212 to validate the identity of the medical care provider and to authenticate the provider device 402 from which the request was received. The medical manager 220 can identify a patient device to which the provider 220 requests access. In some implementations, the medical manager 220 can identify the patient device from the request from the provider device 402. In some implementations, responsive to authenticating the provider device 402, the medical manager 220 can provide a dashboard on a user interface of the provider device through which the medical care provider can access information related to one or more patients of the medical care provider. In some implementations, the medical manager 220 can receive a request to access information related to a patient from the provider device. In some implementations, the medical manager 220 can identify one or more conditions that can cause the medical manager 220 to trigger a notification to the provider device of the medical care provider. The notification can be specific to a particular patient. For example, responsive to the medical manager determining that a patient device is running out of a medication, the medical manager 220 can generate a notification to the provider device of the medical care provider of the patient associated with the patient device 302 to notify the medical care provider to put in a request to refill the prescription medication.

The medical manager 220 can be configured to retrieve or receive information from the patient devices associated with patients subscribed to the medical management system 120. The medical manager 220 can identify, for each patient device 302, which medications are configured to be dispensed via the patient devices, the times at which medications are dispensed, the type and amount of medication in each channel or cartridge of the patient device, as well as other information relating to the patient device. In some implementations, the medical manager 220 can receive location information identifying a location of the patient device, a temperature within each of the medicine cartridges of the patient device, an ambient temperature around the patient device, among others.

The medical manager 220 can be configured to also receive additional information related to each of the patients. In some implementations, the medical management system 120 can communicate with other devices associated with the patient, including wearable devices that may provide physiological feedback or data to the medical management system 120. In some implementations, the wearable devices can measure body temperature, heart rate, breathing rate, oxygen volume, sugar levels, pH levels in fluids, among others.

The medical manager 220 can be configured to communicate with a patient communication device, such as a patient's smartphone or tablet, through which the medical manager 220 can be configured to send notifications to the patient reminding them to take their medications or to perform one or more tasks. In some implementations, the medical manager 220 can be configured to receive data provided by the patient via the patient communication device. In some implementations, the medical manager 220 can establish a communication link with the patient communication device, which can serve as a hub for one or more wearable devices monitoring physiological and other data of the patient as well as the patient device 302.

The medical manager 220 can be configured to actuate one or more components of the patient device 302. In some implementations, the medical manager 220 can be configured to send instructions to the patient device 302, which when executed by a processor of the patient device 302, can cause one or more valves or other actuators of the patient device 302 to dispense medications. In some implementations, the instructions can specify a length of time for which to keep the valves open to ensure that a specific amount of medication is dispensed. In some implementations, the medical manager 220 can be configured to send instructions to regulate the temperature around one or more of the cartridges within which the medications are stored. In some implementations, the medical manager 220 can send instructions to provide cooling to cartridges that include medications that need to be maintained at temperatures below the ambient temperature of the patient device 302 or provide heating to cartridges that include medications that need to be maintained at temperatures above the ambient temperature of the patient device 302.

The medical manager 220 can be configured to maintain and update records for each patient device. In some implementations the medical manager 220 can monitor and track the dispensing of medications to the patient of the patient device. The medical manager 220 can store the medication dispensing activity in one or more databases, such as the patient database. In some implementations, the medical manager 220 can monitor and track a time at which the medication was dispensed, an amount of medication dispensed, physiological and other patient related measurements around the time the medication was dispensed, a location at which the medication was dispensed, among others. In some implementations, the medical manager 220 can store this information each time medication is dispensed. In some implementations, the patient device may take over the function of monitoring and tracking medication dispensing activity and provide the information to the medical manager 220, which can then update the records of the patient device 302 in the patient database 210.

The prescription manager 222 can be configured to manage prescriptions of the patients subscribed to the medical management system 120. The prescription manager 222 can be configured to monitor the amounts of medications remaining in the patient devices such that when one or more medications are running low, the prescription manager 222 can be configured to submit requests to the medical care provider and/or one or more pharmacies to refill the prescription. In some implementations, the prescription manager 222 can be configured to automatically submit requests to pharmacies for refills. In some implementations, the prescription manager 222 can utilize health insurance information of the patient stored in the patient database 210 to submit orders for prescriptions to the pharmacies. The prescription manager 222 can be configured to identify the one or more medications included in each of the cartridges of the patient device. The prescription manager 222 can utilize one or more content sources to determine if any of the medications counteracts with one of the remaining medications in the cartridges or if they include ingredients, compounds, or medications that the patient is allergic to.

Figure 3:
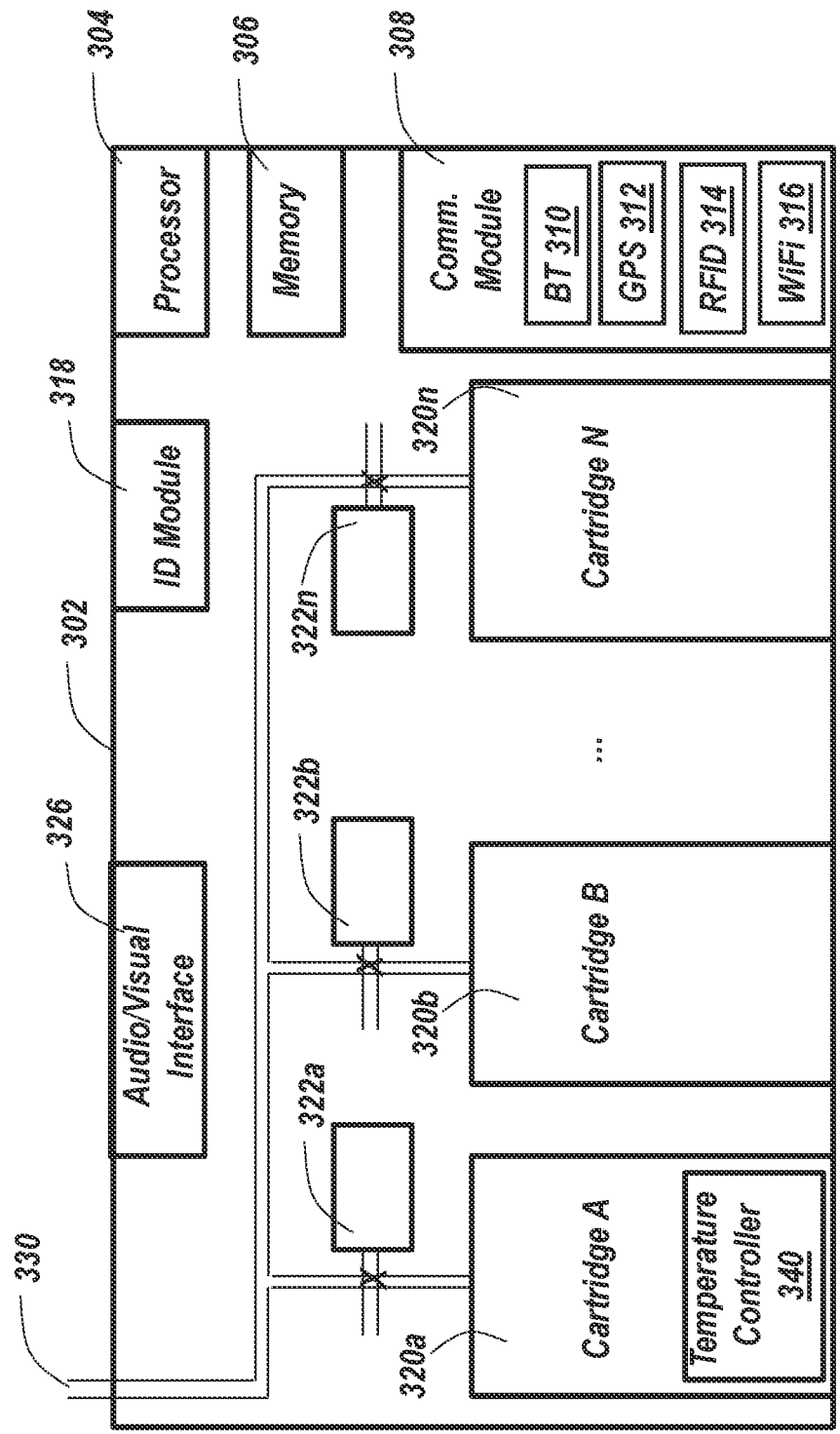
FIG. 3 is a block diagram depicting a patient device configured to dispense medication to a patient.

Referring now also to FIG. 3, FIG. 3 is a block diagram depicting a patient device configured to dispense medication to a patient. The patient device or medical dispensing device 302 includes one or more processors 304, memory 306 and at least one communication module 308. The communication module 308 can include a Bluetooth module 310, a GPS module 312, a RFID module 314 and a WiFi module 316. In some implementations, the communication module 308 can include cellular communications module that allows the medical dispensing device 302 to communicate with the medical management system 120 via cellular networks.

The medical dispensing device 302 can communicate with the medical management system 120 via one or more networks. The medical dispensing device 302 can communicate with the medical management system 120 via Bluetooth, WiFi, a wired interact connection, cellular networks, or other communication channels. In some implementations, the medical dispensing device 302 can communicate with the medical management system 120 using a patient's smartphone or other device as an intermediary. In some implementations, the medical dispensing device 302 can establish a Bluetooth connection with the patient's mobile device and the patient's mobile device can establish a connection with the medical dispensing device 302 via one or more cellular, wired or wireless interact networks. In some implementations in which the medical dispensing device 302 utilizes a Bluetooth network, the medical dispensing device 302 may operate within a communication range of a paired device, for example, a mobile phone, that is in communication with the medical management system 120.

The medical dispensing device 302 also includes an ID module 318 configured to validate communication requests received from other devices. This can serve as a security measure to prevent unauthorized devices from tampering with the medical dispensing device 302 as well as attempting to access health related information of one or more patients that subscribe to the medical management system 120. The ID module 318 can also be configured to validate the identity of the patient to which the medical dispensing device 302 is assigned. In some implementations, the ID module 318 can include a fingerprint reader or scanner to receive fingerprint information from the patient and determine if the received fingerprint information matches the patient. Similarly, the ID module 318 can include an iris scanner to validate the identity of the patient. In some implementations, the ID module 318 can include a camera for facial recognition based on one or more facial features of the patient. In some implementations, the ID module 318 can validate a patient based on voice recognition. In some implementations, the ID module 318 can validate a patient via a communication link established with a trusted device, such as a smartphone or tablet. In some implementations, the patient can be required to enter a passcode or set of unique characters or gestures on a mobile device in communication with the medical dispensing device.

In some implementations, the medical dispensing device 302 may be configured to communicate with a mobile device of the patient to verify the identity of a person accessing or requesting access to the medical dispensing device 302. For instance, the medical dispensing device 302 may only dispense medication in response to receiving a communication or signal from a paired mobile device that can generate the communication or signal upon verifying the identity of the patient. In some implementations, the mobile device can verify the identity of the patient through facial recognition, fingerprint scanning, passwords, or other security measures that can be received, identified or otherwise incorporated via the mobile device. In this way, there is no need for the medical dispensing device 302 to be designed with an integrated fingerprint scanner, camera to detect facial recognition, or keypad to receive a password from the patient, thereby reducing manufacturing costs of the medical dispensing device 302.

The medical dispensing device 302 can be tamper proof. This is to prevent medication abuse and fraud. In some implementations, the medical dispensing device 302 can include an alert system that triggers an alert upon determining that the medical dispensing device 302 has been tampered or an attempt to tamper the medical dispensing device 302 was made. In some implementations, the medical dispensing device 302 can include one or more security modules. The security modules can include hardware and software to ensure that the medication is dispensed to an authorized user or patient. In some implementations, the medical dispensing device can include a user recognition or identification system. In some implementations, the medical dispensing device 302 can include a fingerprint reader, an iris scanner, or any other biometric scanner to confirm the identity of the user. In some implementations, the medical dispensing device 302 can be password protected. In some implementations the medical dispensing device 302 can only be actuated via a second device, such as a smartphone or tablet, registered with the medical management system 120.

In some implementations, the location of the medical dispensing device 302 or the mobile device with which the medical dispensing device 302 can communicate may be monitored. In some implementations, one or more location based policies can be established to ensure additional security. For instance, the medical dispensing device 302 may be configured to only dispense the medicine at predetermined locations, for example, a patient's home, a patient's work location, a hospital or other medical care provider's address, among others. In this way, if the device is stolen or otherwise provided to an unauthorized user, the unauthorized user may be unable to receive medication from the medical dispensing device 302 at locations different from the predetermined locations. In addition, the medical dispensing device 302 may only transmit or receive data from the medical management system 120 at the predetermined locations to reduce security breaches.

The medical dispensing device 302 also includes one or more cartridges 320a-320n (also referred to as cartridge(s) 320) that contain medications to be dispensed. The cartridges 320 can be removable from the medical dispensing device 302. In some implementations, the cartridges 320 can be refilled. The cartridges 320 can be shaped and sized to match an opening in the medical dispensing device 302 and may include one or more identifying labels, tags, or other readable or detectable information that the medical dispensing device 302 can read, identify or otherwise detect to ensure the authenticity of the cartridge 320. This can be used to prevent counterfeit medications or medications provided by unauthorized medical providers. In some implementations, the pharmacy providing the cartridge 320 may include an RFID tag to the cartridge 320 that is encrypted. In some implementations, the cartridge 320 can be tagged in such a way that the cartridge's RFID tag can only be identified by the medical dispensing device 302 associated with the patient for which the medication in the cartridge 320 is prescribed. In some implementations, the cartridge can be made tamper proof such that if an unauthorized attempt to open or otherwise access or damage the cartridge is made, the medication inside the cartridge 320 is destroyed or otherwise tainted or damaged that the medication loses any monetary value to discourage the resale of the medication or the abuse or unprescribed use of the medication. In some implementations, an acid or other compound that destroys the medication may be exposed to the medication.

The medical dispensing device 302 can include one or more slots or channels within which the cartridges 320 are insertable. Each slot can include a temperature controller 340 that is configured to regulate the temperature of the cartridge 320 inserted within the slot. In some implementations, the temperature controller can include a thermoelectric cooler or a heater that can be configured to decrease or increase the temperature of the cartridge 320 or the contents of the cartridge 320.

The medical dispensing device 302 can include one or more actuators 322a-322n (also referred to as actuator(s) 322) that are configured to actuate a switch, valve or other regulator that controls the amount of medication that is dispensed from the respective cartridge 320. The actuators 322 can be configured to allow a certain amount of medication to be dispensed on a per unit time basis. In some implementations, the amount of medication dispensed per unit time may be altered based on various factors, including a size of an opening, the configuration of the actuator, and the amount of time the opening is kept open.

The actuators 322 of the medical dispensing device 302 can be configured to be remotely controlled by the medical manager 220 of the medical management system 120. In some implementations, the medical manager 220 can be configured to provide dosage instructions to the medical dispensing device 302 and the processor 304 can be configured to cause the actuators 322 of the corresponding cartridges 320 to be actuated in such a way that the amount of medications dispensed from the cartridges 320 is equivalent to the desired dosage prescribed by the medical care provider. The actuators 322 can be electronically controlled. In some implementations, the actuators 322 can be powered via an on-board battery. In some implementations, the on-board battery can be rechargeable.

In some implementations, the medical dispensing device 302 can operate using batteries. In some implementations, the batteries may be rechargeable or disposable. In some implementations in which the batteries are rechargeable, the batteries may be charged via a USB cable, via a power supply channel, or via wireless induction. In some implementations, to implement wireless induction, the medical dispensing device can be incorporated with a wireless charging coil, for example, a wireless charging coil supplied by DIGIKEY and manufactured by Wurth Electronics, Inc. In some implementations, the wireless charging coil can be Part Number 76030811, manufactured by Wurth Electronics, Inc. The shape, size and position of the one or more wireless charging coils can be designed to fit within the medical dispensing device.

The medical dispensing device 302 can include one or more sensors for sensing or monitoring the amount of medication dispensed from (or remaining in) each of the cartridges 320. In some implementations, the sensors can monitor a weight of medication dispensed or a weight of medication remaining in the cartridge 320 after medication is dispensed. In some implementations, the sensors can count a number of pills dispensed. In some implementations, the sensors can monitor a time for which a valve is left open and a flow rate of the medication flowing through the valve. The medical dispensing device 302 can include sensors measuring a quantity of medication remaining in the medical dispensing device 302. In some implementations, the medical dispensing device 302 can determine an amount of medication remaining in the medical dispensing device 302 based on the amount of medication included in a medicine cartridge 320 and an amount of medication already dispensed since the medicine cartridge was first inserted. The medical dispensing device 302 can be configured to communicate medicine quantity levels to the medical management system 120 such that the medical management system 120 can submit orders for refills to one or more pharmacies before the medicine cartridge 320 is completely empty.

The medical dispensing device 302, via the processor 304, can maintain a monitoring log storing information related to the monitoring of the medical dispensing device 302. The monitoring log can store information related to communications received from the medical management system 120. The log can store event related information. Examples of events include a medicine dispensing event, a medical care provider device 402 or medical management system 120 establishing communications with the medical dispensing device 302, an alarm triggering event (in the event of an attempt to tamper the medical dispensing device 302), location changes of the medical dispensing device 302, changes to ambient conditions of the medical device 302, for example, when the medical dispensing device senses a temperature below or above one or more predefined temperatures, detecting low medication levels in one or more cartridges of the medical dispensing device 302, among others. The activity logs can identify a date and time at which medication was dispensed, a dosage of medication dispensed as well as any other physiological measurements, for example, temperature, pulse, heart rate, blood pressure, sugar levels, among others, taken around the time the medication was dispensed. In addition to medication dispensing related activity, the activity logs can identify when a medical care provider communicated with the medical dispensing device 302. In some implementations, the activity logs can include information related to dosage changes as well as changes in the time at which medication is to be administered.

The medical dispensing device 302 includes an outlet port or opening 330 through which medications within the cartridges 320 are dispensed from the medical dispensing device 302. The outlet opening 330 can be configured to allow a patient to administer the medication orally. In some implementations, the opening 330 can be configured to allow medication to be dispensed in such a way that a patient can apply the medication topically, subcutaneously, pulmonary or intravenously, among others.

The patient device, otherwise referred to as a medical dispensing device 302 can be configured to allow a medical care provider, for example, a doctor, the ability to remotely monitor, regulate and manipulate medication administration to a patient associated with the patient device. Through the medical dispensing device 302, the medical care provider can adjust either the dosage of medications or the time at which the medication is administered. In some implementations, the medical care provider may receive feedback through the medical dispensing device or other medical device monitoring the patient and adjust the dosage or time at which to administer medication based on the received feedback. The medical dispensing device 302 can be equipped with a communications module that is configured to communicate with the medical management system 120 through which the medical care provider can remotely communicate with the medical dispensing device 302. The communications module can include both hardware and software components that allow the medical dispensing device 302 to receive and transmit instructions and information. In some implementations, the communications module can be configured to provide wireless communications, for example, BLUETOOTH, WiFi, cellular communications, NFC, among others. In some implementations, the communications module can be configured to communicate with another device, such as a smartphone, tablet, or other device that allows the medical dispensing device 302 to receive and execute instructions received from the medical care provider.

In some implementations, the medical dispensing device 302 can include a temperature control module to control the temperature of medication within the medical dispensing device 302. In this way, if the medicine in the medical dispensing device 302 is to be maintained at a particular temperature, and the medical dispensing device 302 is in a location that has an ambient temperature much higher than the temperature at which to maintain the medicine, the medical dispensing device 302 can provide cooling to the medication. Conversely, the medical dispensing device 302 can provide heating to medications that are supposed to be stored or maintained at temperatures higher than the ambient temperature at which the medical dispensing device 302 is located.

In some implementations, the medical dispensing device 302 can include a thermoelectric cooler, such as one manufactured by CUSTOM THERMOELECTRIC of Bishopville, MD, USA. In some implementations, the thermoelectric cooler can be Part #03201-9G30-08RA manufactured by CUSTOM THERMOELECTRIC or other similar thermoelectric cooler. In some implementations, the medical dispensing device 302 can include one or more heat or cooling tanks that may be positioned adjacent to or around one or more cartridges of the medical dispensing device 302. In some implementations, the heating or cooling mechanism can use convection, conduction or radiation. In some implementations, a small convection system may be used to carry air from the thermoelectric cooler to a top portion of the medical dispensing device 302 where the air will be dispersed to the atmosphere. As such, the medical dispensing device 302 may include one or more vents through which air can enter and exit the medical dispensing device 302.

In some implementations, the thermoelectric cooler can be part of the medical dispensing device 302. In some implementations, the thermoelectric cooler can be part of the cartridge 320 that may be removable from the medical dispensing device 302. In some implementations in which the thermoelectric cooler is part of the cartridge, the thermoelectric cooler can be positioned within the cartridge 320 in such a way that when the cartridge 320 is inserted in the medical dispensing device 302, the thermoelectric cooler can be coupled to a power source of the medical dispensing device 302 that can provide power to the thermoelectric cooler. In some implementations in which the thermoelectric cooler is part of the medical dispensing device 302, the thermoelectric cooler can be configured or positioned in such a way that the thermoelectric cooler can provide heating or cooling to the cartridge and its contents.

In some implementations, the medical dispensing device 302 can utilize a fluid channel that includes a thermally conductive fluid, such as alcohol. The fluid channel can be positioned to extend along a side of the medical dispensing device 302. The fluid channel can be configured to cause heat to dissipate from around the cartridges 320. In some implementations, the fluid channel can be configured to provide a cooling effect similar to how laptop coolers dissipate heat generated by laptops.

In some implementations, a temperature sensor positioned within, near or adjacent to the cartridges 320 can detect the ambient temperature around the cartridge 320. In some implementations, the ambient temperature may be based on weather databases based on location. In some implementations, the location of the medical dispensing device 302 can be determined from a GPS module or cellular module of the medical dispensing device 302. In some implementations, the medical dispensing device 302 can be configured or otherwise programmed to activate the cooling or heating systems of the medical dispensing device 302 to maintain the temperature around the cartridges 320 at temperatures suitable for storing the medications.

In some implementations, the medical dispensing device 302 can include one or more audio output components, such as a speaker, configured to emit alerts or transmit voice commands to the patient. In some implementations, the medical dispensing device 302 can communicate with a wireless or wired headphone or speaker to provide voice or audio notifications to the patient. In some implementations, the medical dispensing device 302 can include a microphone through which the patient can communicate with a medical care provider. In this way, patients that had vision or hearing impaired, may be able to locate the medical dispensing device 302 as well as receive instructions from a medical care provider remotely. In some implementations, the medical dispensing device 302 can include a screen through which a patient who has impaired heating can receive instructions.

In some implementations, the medical dispensing device 302 can also be configured to include one or more input channels through which the medical dispensing device 302 can receive input data from one or more wearable or portable measurement devices measuring physiological and other metrics of the patient. The data received from the measurement devices can be used by the medical dispensing device 302 to administer medication to the patient. In some implementations, the medical dispensing device 302 can utilize one or more medicine administration policies according to which dosages are administered. These policies can be established by a medical care provider of the patient and provided to the medical dispensing device 302 via the medical management system 120.

In some implementations, the medical dispensing device 302 can be configured to report the measured data to the medical management system 120. The medical dispensing device 302 can report the measured data periodically or upon a detected triggering event (for example, if the blood sugar level drops below a certain level, or a pulse rate or breathing rate drops below or exceeds a predefined level). The medical management system 120 can be configured to identify triggering events based on the data received and may initiate a communication with the medical care provider alerting the provider of a medical condition.

The medical care provider, via the provider device 402, can send instructions to the medical dispensing device to administer medication to the patient. In some implementations, the provider device 402 can modify a dosage regimen programmed for the medical dispensing device by sending instructions to the medical dispensing device 302 via the medical management system 120.

Figure 4:
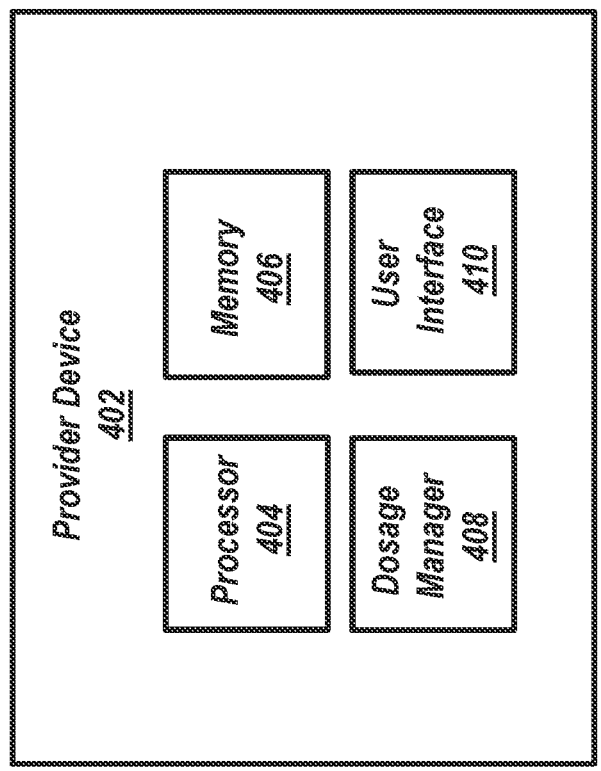
FIG. 4 is a block diagram depicting a provider device configured to allow a medical care provider to manage medications of patients receiving medication through the patient device of FIG. 3.

FIG. 4 is a block diagram depicting a provider device configured to allow a medical care provider to manage medications of patients receiving medication through the patient device of FIG. 3. The provider device 402 can include a processor 404, a memory 406, a dosage manager 408 and a user interface 410.

The dosage manager 408 can be configured to manage, administer and monitor dosage information provided to each of the medical dispensing devices 302 of patients of the medical care provider of the provider device 402. The dosage manager 408 can include hardware, software or a combination of both to communicate with each of the medical dispensing devices 302 via the medical management system 120. The dosage manager 408 can receive instructions from the medical care provider via the user interface 410, which can be provided for display on a display of the provider device 402. The provider can view patient related data on the user interface, including but not limited to current dosage levels of medications, the identity of medications loaded in the cartridges 320 of the medical dispensing device 302, as well as data from one or more monitoring devices monitoring patient's vitals, physiological metrics, among others. The provider can send instructions to administer, modify or otherwise alter dosages to the medical dispensing devices 302. The dosage manager 408 can receive these instructions and provide instructions to the medical management system 120 such that the correct dosage can be administered at the medical dispensing device 302.

C. Systems and Methods of Remote Medication Management and Monitoring

Figure 5:
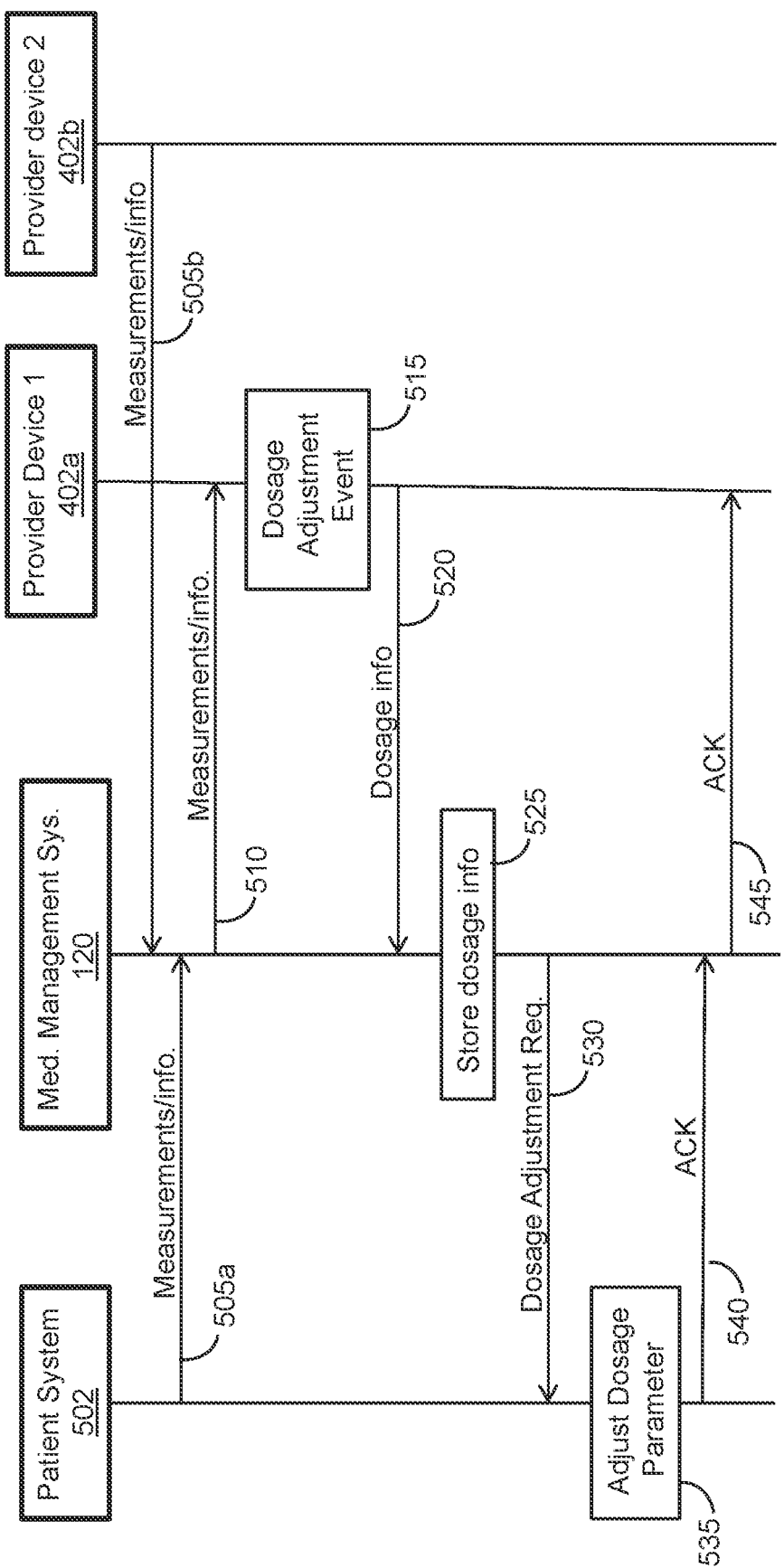
FIG. 5 is a communication flowchart illustrating communications of the medical management system with a patient system and provider devices in a process for remote monitoring of medication.

FIG. 5 is a communication flowchart illustrating communications of the medical management system 120 with a patient system 502 and provider devices 402*a* and 402*b* in a process of remote monitoring of medication. Referring now to FIGS. 2-5, the communications can include the medical management system 120 receiving measurements information and/or other medication related information (stage(s) 505*a* and/or 505*b*), the medical management system 120 forwarding the received information to the provider device 402*a* (stage 510), the provider device 402*a* determining a dosage adjustment event based on the received data (stage 515), the provider device 402*a* sending an indication of a dosage adjustment to the medical management system 120 (stage 520), the medical management system 120 storing data indicative of the dosage adjustment (stage 525) and forwarding the indication of the dosage adjustment to the patient system 502 (stage 530), the patient system 502 adjusting a dosage parameter (stage 535) and sending an acknowledgement message to the medical management system 120 (stage 540), and the medical management system 120 forwarding the acknowledgement message to the provider device 402*a* (stage 545).

The patient system 502 can send measurement data and/or other information to the medical management system 120 (stage 505*a*). In some implementations, the patient system 502 can include a medical dispensing device 302 capable of sending information directly to the medical management system 120, e.g., through cellular or WiFi communication. In some implementations, the patient system 502 can further include a patient communication device, such as a mobile device, portable device, wearable device or computer device, communicatively coupled to the medical dispensing device 302 and the medical management system 120. The patient system 502 can include capabilities for measuring vitals or physiological metrics of a patient. For instance, the medical dispensing device 302 can include sensors or sensing modules for performing such measurements, or the patient system 502 can include wearable or portable measuring devices that can be communicatively coupled with the medical dispensing device 302 or the patient communication device.

The patient system 502 can send, to the medical management system 120, patient system related information. The patient system related information can include an indication of physiological or vital measurements taken by or received by the patient system, indication of a medication level, indication of an attempt to tamper the medical dispensing device 302, indication of a medication dispensing event, indication of ambient condition(s) associated with the medical dispensing device 302, indication of medication expiration, or a combination thereof. The information sent by the patient system 502 can also include an indication of a location and/or an identification of the patient or a device thereof. The vital or physiological measurements can include body temperature measurement, blood pressure measurement, pulse measurement, blood sugar measurement, blood oxygen level measurement, heart beat measurement, or a combination thereof.

The medication level can include a level of consumed medication or a level of medication remaining in one or more cartridges 320. The indication of an attempt to tamper the medical dispensing device 302 can be in the form of one-bit signal or can include information indicative of a type of tampering, time of tampering attempt, result of tampering attempt or a combination thereof. The indication of a medication dispensing event can include information indicative of occurrence of a dispensing event, such as one-bit signal, information indicative of a dispensed medication dosage (or amount), time of dispensing event, location of dispensing event or a combination thereof. In some implementations, the patient system 502 can be configured to report each dispensing event to the medical management system 120. The medical management system 120 can be configured to log information indicative of dispensing events, such as dispensing event timing, dispensing event location, amount of dispensed medication or a combination thereof. For instance, the medical manager 220 can store such information in the memory 206 or in association with the patient database 210.

The indication of ambient condition(s) associated with the medical dispensing device 302 can include information indicative of ambient temperature or ambient humidity level inside or around the cartridges 320. Such ambient information can be acquired through ambient sensors associated with, or coupled to, the medical dispensing device 302. The indication of medication expiration can include information indicative of an expiration date, information indicative of changes in characteristics, such as chemical composition, of the medication, or a signal, such as a one-bit signal, indicating that the medication already or most likely expired. For instance, if the processor 304 detects that ambient conditions associated with the medication in a cartridge 320 are at a level (e.g., ambient temperature higher than a respective temperature threshold or ambient humidity higher than a respective humidity level threshold) that can alter the potency of the medication, the processor 304 can determine the medication to be expired and cause an indication of such expiration to be sent to the medical management system 120.

In some implementations, the medical management system 120 can receive information indicative of medical test results, medical imaging results or physiological measurements associated with the patient from the provider device 402b (stage 505b). The provider device 402b can be associated with a provider such as a medical lab, medical imaging facility, hospital or any other medical service provider or facility. For instance, the patient can visit a medical lab for performing a blood test. Once the blood test results are available to the provider device 402b (e.g., a computer device associated with the medical lab), the provider device 402b can send the blood test results to the medical management system (stage 505b). The provider device 402b can send information identifying the patient or a device thereof.

Upon receiving the information from the patient system 502 and/or the provider device 402b, the medical management system 120 can forward the received information or a portion thereof to the provider device 402a (stage 510). The provider device 402a can be associated with a medical doctor, a hospital or other medical provider. The medical management system 120 can process the received information prior to forwarding such information to the provider device 402b. For instance, the medical management system 120 can scan the received information to locate a device identifier (IL)), such as an ID of the medical dispensing device 302. The medical management system 120 can identify the patient based on the device ID and insert an identification of the patient, such as patient's name, a patient account number, or a combination thereof, in the information forwarded to the provider device 402a. The medical management system 120 can access the patient database 210 and/or the prescription manager 222 to identify the patient based on the device ID. Based on the identified patient, the medical management system 120 can identify a provider (or a device thereof) to whom (or to which) to forward the received information. For instance, the medical management system 120 can access the patient database 210, the prescription manager 222 and/or the provider database 212 to identify the provider. The medical management system 120 can be configured to store the information received from patient system 502 or the provider device 402b in a database associated with the medical management system 120.

The provider device 402b can provide the information received from the medical management system 120 at stage 510 for presentation, e.g., through a respective user interface 410, to a user such as a doctor, a nurse, a pharmacist or other medical professional. The medical professional can determine a need to adjust the dosage of the medication based on the information provided by the provider device 402b. Adjusting the medication dosage can include the medical professional changing the amount of medication dispensed at each consumption, changing a number of times the medication is dispensed to the patient, changing the timing for dispensing the medication or a combination thereof. The medical professional can also decide to stop providing the medication to the patient, prescribe a new medication, prescribe the same medication again, request medical test to be performed for the patient, arrange for an appointment with the patient or a combination thereof.

According to a first scenario, the medical professional can determine a change (or no change) to the patient's condition based on patient's blood test results, vital signs measurements, medical imaging data or other physiological measurements, and decide accordingly to increase (or decrease) the medication dosage for the patient. For instance, the medical professional can increase the medication dosage upon determining that a lack of significant improvement in the patient's condition. The medical professional can decide to decrease the medication dosage upon determining an improvement in the patient's condition.

According to a second scenario, the medical professional can diagnose the patient for an allergic or side effect reaction based on medical information presented by the provider device 402a and decide to reduce the medication dosage or halt medication consumption by the patient. The medical professional may decide to prescribe another medication for the patient, make a request for (additional) medical tests to be performed, arrange for an appointment with patient or a combination thereof.

According to a third scenario, the medical professional can determine that the amount of medication consumed by the patient so far reached a certain level, and in response decide to adjust the medication dosage. For instance, for some medications, the dosage needs to be increased gradually in the beginning of a treatment and reduced gradually at the end of the treatment.

According to a fourth scenario, the medical professional can determine that the medication may have expired or the medication potency may have been affected by undesired ambient conditions recorded by sensors associated with the medical dispensing device 302. For instance, if the medication is to be kept refrigerated below a threshold temperature and the information presented to the medical professional indicates temperature value(s) substantially higher than the threshold temperature, the medical professional may determine that consumption of the medication may be dangerous for the patient. In response, the medical professional can decide to stop dispensing medication from the cartridges 320 by the medical dispensing device 302. The medical professional can prescribe the same (or another) medication to the patient.

The scenarios described above are provided for illustration purposes. Other scenarios may be contemplated based on the description above. Also, the described scenarios are not mutually exclusive. That is, the information received by the provider device 402a can be indicative of more than one scenario.

Upon making a decision to adjust the medication dosage or halt medication dispensing, the medical professional can input an indication of the medication dosage adjustment (or the adjusted medication dosage) to the provider device 402a through the user interface 410. The input indication can include a medication amount, a number of times the medication is to be consumed per day, timing information for medication consumption or a combination thereof. A halt of medication dispensing can be indicated by a zero medication dosage or through a respective instruction to block the medical dispensing device 302 from dispensing anymore medication from the cartridges 320. The medical professional can also input indication(s) of a new prescription, request for medical test(s), appointment with the patient or a combination thereof. The provider device 402a can determine the need for adjusting medication dosage or halting medication dispensing based on the input from the medical professional (stage 515).

In some implementations, the provider device 402a can automatically analyze the information received from the medical management system 120 at stage 510 and determine whether or not to adjust medication dosage (stage 515). For instance, the third scenario described above can be handled automatically by the dosage manager 408 associated with the provider device 402a or the medical manager 222 (or prescription manager 220) associated with medical management system 120. The dosage manager 408, the medical manager 220 or the prescription manager 222 can compare a medication consumption amount value to respective medication amount values stored in a lookup table (LUT) and decide whether or not to adjust medication dosage. Similar automatic determination regarding medication dosage adjustment can be implemented for one or more other scenarios. In some implementations, automatic decisions to adjust medication dosage can be reviewed and approved by a medical professional before such adjustment is provided for execution to the medical dispensing device 302 (or any other patient device).

In general, the dosage manager 408 can retrieve (or read) physiological measurement values, amount of dispensed medication, ambient condition measurements, etc., from the information received from the medical management system 120 at stage 510 and compare the retrieved values (or values computed based on the retrieved values) to corresponding threshold (or range) values store in the LUT. The dosage manager 408 can then make a recommendation, for instance, through the user interface 410, for the medical professional to change medication dosage based on the performed comparison(s). The recommendation can include an indication of a new dosage, a dosage adjustment or simply a flag or message indicating a potential need for adjusting medication dosage. The dosage manager 408 can retrieve a value indicative of the new dosage or the dosage adjustment from the LUT. In some implementations, the medical manager 220 (or the prescription manager 222) can compare the physiological measurement values, amount of dispensed medication, ambient condition measurements, etc., obtained from patient system 502 or the provider device 402b to corresponding values in the LUT and make a recommendation for adjusting medication dosage. In some such implementations, the medical management system 120 can send the recommendation to the provider device 402a for presenting to the medical professional. In some implementations, the medical management system 120 can use the recommendation to automatically generate a request to adjust the medication dosage and transmit the request to the patient system 502.

The provider device 402a can be configured to send indication(s) of the medication dosage adjustment, new prescription(s), appointment arrangement(s) or medical test request(s) input by the medical professional the medical management system 120 (stage 520). The provider device 402a can include an identification of the patient with the information sent to the medical management system 120. Upon receiving the information, the medical management system 120 can identify the respective patient based on the patient identification. The medical management system 120 can store the received information, or a portion thereof, in a database or memory 206 associated with the medical management system 120 (stage 525). For instance, the information can be stored in association with the patient database 212, the medical manager 220 the prescription manager 220 or a combination thereof.

The medical management system 120 can be configured to send one or more dosage adjustment instructions to the patient system 502 based on the information received from the provider device 402a (stage 530). Such instructions can include indication(s) of a medication amount (or change thereof), number dispensing times per day (or change thereof), dispensing timing information or a combination thereof. The medical system 120 can also send indication(s) of new prescription, requested medical test(s) or requested appointment(s) to the patient system 502. In some implementations, the medical management system 120 can forward an indication of received prescription(s) or received medical test request(s) to another provider device, such a device associated with a pharmacy, a medical lab or other medical service facility.

Upon receiving the dosage adjustment instruction at stage 530, the patient system 502 can take the proper steps for adjusting medication dispensing to the patient (stage 535). For instance, if the instruction is received by a mobile or other communication device (other than the medical dispensing device 302), the receiving device can forward the instruction to the medical dispensing device 302. Upon receiving the instruction, the medical dispensing device, or a circuit thereof, can change at least one dispensing parameter to cause the dosage adjustment indicated in the received instruction. In some implementations, the medical dispensing device 302 can be controlled by the mobile (or other communication) device, in which case, the mobile device can send the at least one dispensing parameter to the medical dispensing device 302. In response to the change to the at least one parameter, the actuators 322 can dispense medication according to the new dosage. For instance, the processor 304 can adjust the amount of medication dispensed from the cartridge(s) 320 per unit time by modifying respective opening size(s), configuration(s) of the respective actuator(s) 322, an amount of time the opening(s) is/are kept open or a combination thereof. The processor 304 can make the adjustment(s) so that when the actuators 322 are actuated, the amount of medication dispensed from the cartridges 320 is equal to new (or adjusted) dosage.

Once, the medication dispensing parameter(s) is adjusted (or modified), the patient system 502 can send an acknowledgment that the adjustment is executed to the medical management system 120 (stage 540). In some implementations, the medical management system 120 can also send an acknowledgement to the provider device 402a (stage 545) indicating that the dosage adjustment is in effect. In some implementations, the acknowledgement(s) associated with stage 540 and/or stage 545 can be optional. For instance, the medical management system 120 can check that the new dosage is in effect when a report of a following dispensing event is received from the patient system 502. Such report can include the amount of medication dispensed during the dispensing event and the medical management system 120 can compare the amount of medication dispensed to the new (or adjusted) dosage.

D. Systems and Methods of Supply Chain Management

Figure 6:
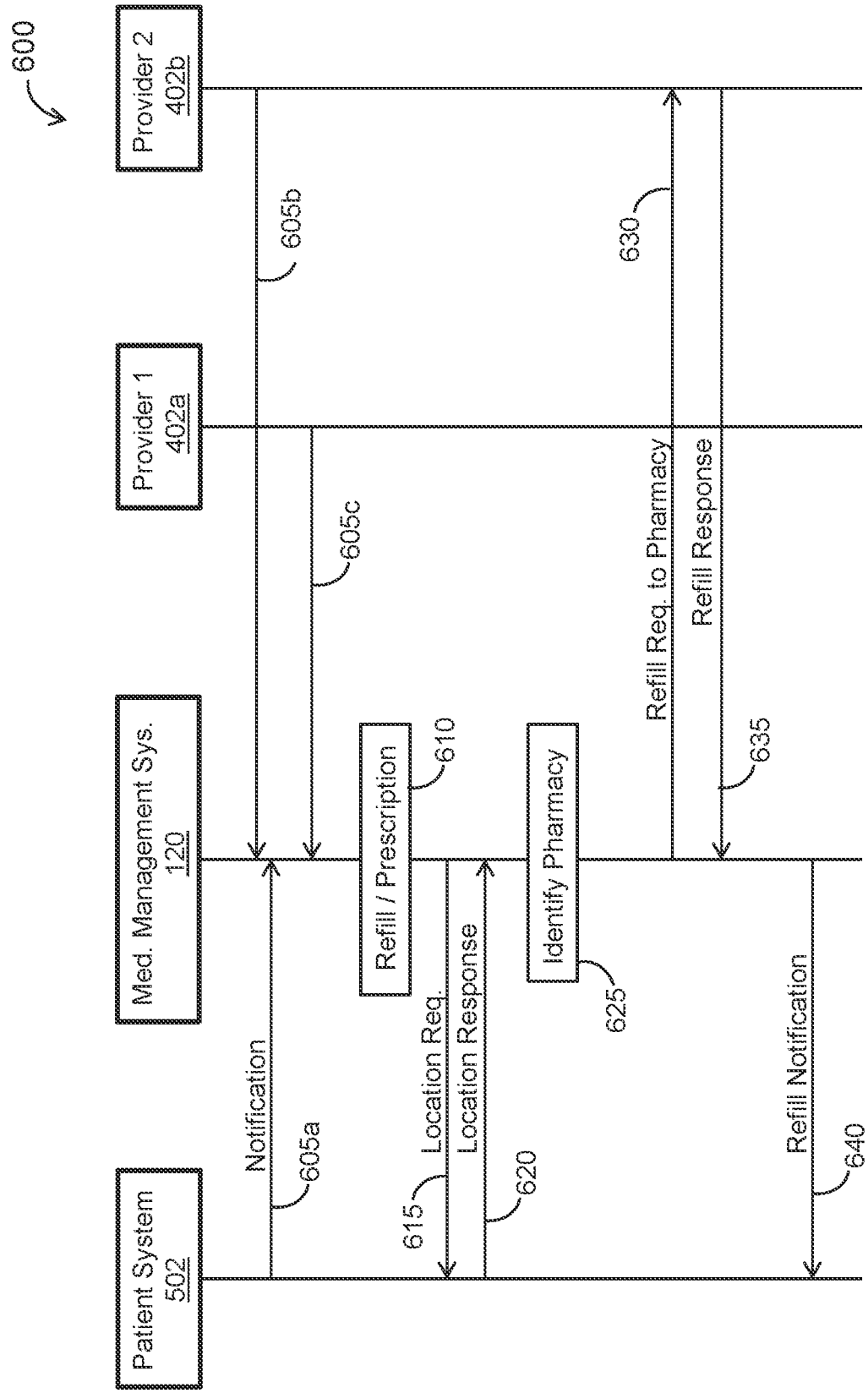
FIG. 6 is a sequence diagram illustrating communications and processing flow involved in a method for managing a supply chain for supplying a patient with respective medication.

FIG. 6 is a sequence diagram illustrating communications and processing flow involved in a method 600 for managing a supply chain for supplying a patient with respective medication. Referring now to FIGS. 2-4 and 6, the method 600 can include the medical management system 120 receiving a notification from the patient system 502 (communication 605a) or from provider device(s) 402a and/or 402b (communication(s) 605ab and/or 605c) and determining a medication refill event based on the received notification (processing step 610). The method 600 can include the medical management system 120 obtaining information indicative of patient's location (communications 615 and 620) and identifying a medical service provider (processing step 625). The method can also include the medical management system 120 requesting medication supply, or refill, from a provider device 402b associated with the identified pharmacy (communication 630) and receiving an acknowledgement response from the provider device 402b (communication 635). The medical management system 120 can send a notification indicative of medication supply or refill to the patient system 502 (communication 640).

The method 600 can include the patient system 502 sending a notification (communication 605a) including information that can cause the medical management system 120 to trigger a medication refill or medication supply process. The notification 605a can include information indicative of a dispensing event, an amount of medication dispensed by the medical dispensing device 302, an amount of medication remaining in the medical dispensing device 302 or cartridges 320 thereof, the amount of medication in the medical dispensing device 302 being below a given threshold, a medication refill request or a combination thereof. If the notification 505a includes an indication of dispensing event or an amount of medication dispensed in association with a dispensing event, the medical manager 220 (or the prescription manager 222) can use such indication to calculate the amount remaining in the medical dispensing device 302 or cartridges 320 thereof.

The medical management system 120 can receive a notification 605b from a provider device 402b associated with a pharmacy or other medical service provider. The notification 605b can include information indicative of expiration (or change in characteristics) of the medication in the medical dispensing device 302 or cartridges 320 thereof a medication refill date or a combination thereof. For instance, as discussed with regard to FIG. 5, the medical management system 120 may send an indication of an expiration date or measurements data (e.g., ambient measurements, or other sensor data) provided by the medical dispensing device 302 to the provider device 402b. A medical professional associated with provider device 402b may determine, based on such data, that the medication in the cartridge(s) 320 is no longer valid for consumption. In response, the provider device 402b can send the notification 605b to the medical management system 120 indicating that the medication in the medical dispensing device 302 of the patient is no longer valid for consumption.

The medical management system 120 can receive a notification 605c from a provider device 402a associated with a medical doctor or a hospital. The notification 605c can include indication of a new medication refill or a new prescription. For instance, as discussed with regard to FIG. 5, the provider device 402a can receive information indicative of medical tests and/or physiological measurements associated with the patient, an amount of medication dispensed by the medical dispensing device 302, sensor data provided by the medical dispensing 302 or a combination thereof. A medical doctor associated with the provider device 402a can prescribe a new medication and/or a medication refill for the patient based on the received information. The provider device 402a can then send the notification 605c to the medical management system 120 indicating the new medication prescription and/or medication refill. In some instances, the notification 605c can include a reminder of an approaching medication refill date.

In some instances, responsive to a doctor visit by the patient, the doctor (or other medical professional) can enter a medical prescription into the provider device 402a (e.g., through a respective user interface 410) and cause the prescription to be sent to the medical management system. For example, the medical dispensing device 302 may be initially provided (with little or no medication) to the patient by a doctor (or other medical professional) upon a doctor visit or a visit to a medical facility. In such an example, the notification 605c can include indication(s) of the prescribed medication, an identification of the patient, an identification of the medical dispensing device 302, a phone number (or identification of a communication device) associated with the patient or a combination thereof. Upon receiving the notification 605c, the medical management system 120 can register the medical dispensing device in association with the patient into the patient database 210.

Upon receiving the notification(s) 605a, 605b and/or 605c, the medical management system 120 can determine a medication supply (or refill) process. Actions performed by the medical management system 120 to detect a medication supply event and/or initiate a medication supply process can differ based on the received notification(s) (e.g., 605a, 605b or 605c), if any, and the information in the received notification(s). For example, the notification 605a received from the patient system 502 can be indicative of a recent medication dispensing event. That is, the medical dispensing device 302, or a patient communication device paired thereto, can be configured to report each medication dispensing event to the medical management system 120.

Upon receiving such notification 605a by the medical management system 120, the medical manager 220 and/or the prescription manager 222 can update one or more parameters indicative of total medication amount dispensed since a given date or event, total medication remaining in the medical dispensing device 302 or a cartridge 320 therein, number of dispensing events or a combination thereof. The medical manager 220 and/or the prescription manager 222 can compare the updated parameter(s) to one or more respective threshold values to determine a medication refill event. For instance, if the amount of medication remaining in the medical dispensing device 302 or a cartridge therein is below a respective threshold (or the amount of medication dispensed since a given date or event is above another respective threshold), the medical manager 220 and/or the prescription manager 222 can determine that a medication refill is needed before the patient is run out of medication.

In some implementations, a received notification 605a or 605b can include an indication of an approaching medication refill date or a medication refill request. In response, the medical manager 220 and/or the prescription manager 222 can check a medication refill date maintained at the medical management system 120 (or compare the received date to a respective date stored by the medical management system 120). The medical manager 220 and/or the prescription manager 222 can then determine a refill event based on the date checking (or date comparing).

In some implementations, the medical manager 220 and/or the prescription manager 222 can determine a medication supply or refill event based on data maintained by the medical management system 120 and not necessarily in response to a received notification. For example, the medical manager 220 and/or the prescription manager 222 can determine a refill date based on information previously provided by a medical professional (e.g., refill date provided in a respective prescription on record or by a pharmacist who previously supplied the medication) or through prediction based on a monitored rate of dispensing the medication by the medical dispensing device 302. For instance, the medical manager 220 and/or the prescription manager 222 can record instances of medication dispensing activities or events based on communications 505a and/or 605a received from the patient system 502. In some implementations, the patient system 502 report each medication dispensing event to the medical management system 120. Reporting of medication dispensing events can be on event basis (e.g., immediately after medication is dispensed by the medical dispensing device 302), daily basis, hourly basis, or according other time frame.

The medical manager 220 and/or the prescription manager 222 can estimate a dispensing rate (e.g., amount of medication dispensed on a daily basis) based on history of recorded dispensing events and/or information indicative of medication amount dispensed per event. The estimate dispensing rate can be computed as an average of amount of medication dispensed (e.g., per day) for the last n days where n is an integer. The medical management system 120 can obtain and store information indicative of the amount of medication dispensed at each dispensing event from communications 505a and/or 605a reporting dispensing event, based on configuration parameters of the medical dispensing device 302 or from a respective prescription. The medical manager 220 and/or the prescription manager 222 can use the estimated dispensing rate and information indicative of cartridge capacity to predict a potential supply/refill date. For instance, the medical manager 220 can divide the capacity of a single cartridge 320 (or cumulative capacity of all cartridges 320 in the medical dispensing device) by the estimated dispensing rate to calculate a duration (e.g., number of days) to consume the medication. The medical manager can set the supply/refill date few days (e.g., a week, five days or other time period) prior to complete consumption of medication in a single cartridge 320 or in all cartridges 320.

In some instances, determining the medication supply or refill event (processing step 610) can include the medical manager 220 requesting and receiving approval from the patient's doctor (or other medical professional). For instance, if the medication supply event is determined based on information stored by the medical management system 120 or provided by the patient system 502, or if a prescription or doctor approval is needed, the medical manager 220 can send a request for approval (or for a prescription) to the provider device 402a. Upon receiving approval (or the requested prescription), the medical management system 120 can proceed to initiate a medication supply process.

In some instances, the medical management system 120 can determine a medication supply or refill event based on a notification 605c received from a provider device 402a associated with a doctor of the patient. For instance, as discussed with regard to FIG. 5, upon the provider device 402a receiving medical test(s) data, physiological measurement(s) data or other sensor data associated with the patient or the respective medical dispensing device 302, the doctor can generate a new prescription or a refill request for sending to the medical management system 120. The medical manager 220 and/or the prescription manager 222 can determine a medication supply or refill event based on the received request or prescription.

In instances where a new prescription is received by the medical management system, the prescription manager 222 can store data indicative of the received prescription in the medical management system 120 or a database associated thereto. In some implementations, the prescription manager 220 can delete data associated with previous prescriptions and keep data associated with the recent prescription. In some implementations, the prescription manager can manage a data field indicative of which prescriptions are active and which ones are inactive. For instance, once receiving a new prescription, the prescription manager 222 can flag the new prescription (e.g., through a respective data field) as active. A prescription can be kept active until all respective refills are executed, the prescribed medication is completely dispensed by the medical dispensing device 302, a request to inactivate the prescription is received from the doctor (or other medical professional), a request to stop dispensing the medication to the patient is received from the doctor (or other medical professional), a new prescription (e.g., prescribing the same or alternative medication) is received, or a respective expiration date passes. The prescription manager 222 can be configured to initiate medication supply processes for medication associated with an active prescription. The medical prescription manager 222 can cause the medical manager 220 to send notification(s) indicative of inactivation of a prescription to a patient's doctor (e.g., to provider device 402a). The medical doctor (or other medical professional) can then determine whether or not to generate a new prescription for the patient.

The medical management system 120 can send a request for patient location to the patient system 502 (communication 615) and receive a location response including information indicative of a current location of the patient (communication 620). In some implementations, the medical management system 120 can send the request 615 to the medical dispensing device 302 associated with the patient, if the medical dispensing device 302 is equipped with global positioning system ((IPS) (or other location identification) capabilities. In some implementations, the medical management system 120 can send the request 615 to a mobile device (or other communication device) associated with patient. The medical management system 120 can be configured to send the request 615 on a regular (or periodic) basis, in response to determination of a medication supply or refill event (processing step 610) or a combination thereof.

Referring back to FIG. 2 and Section B above, the medical management system 120 also includes a patient location manager 215. The patient location manager 215 can be configured to collect or obtain patient location information from one or more sources on a regular basis or in response to specific events (such as determination of a medication supply event), maintain and/or update patient location data for each patient (or a subset of patients), provide patient location data to other entities (such as medical manager 220 or prescription manager 222), analyze patient location data over periods of time to determine patient location trends or a combination thereof. The medical management system 120 can receive patient location information on hourly basis, daily basis, event basis (e.g., in each communication 505a or 605a front the patient system 502). In some implementations, the medical management system 120 can also obtain patient location information through communications from medical service providers.

The patient location manager 230 can apply a location determination policy to determine which locations are locations of interest. The location determination policy can include one or more rules for determining whether a given location is of interest (e.g., worth recording as a separate location or considering when handling medication supply/refill events). The rules can include (i) a threshold for a period of stay by the patient at any detected location, (ii) frequency of visiting detected location and/or (iii) distance from a permanent address associated with the patient. The patient location manager 230 can determine, based on recorded patient location data and the location determination policy, that the patient is usually in a first location (e.g., specific address, town, city or state) during a first period (e.g. specific season, month or interval of dates) of the year and in a second location during a second period of time.

The patient location manager 215 can be configured to maintain a list of sources or message types from which patient location information can be requested, obtained or retrieved. For instance, notifications (such as notification(s) 505a, 505b, 605a, 605b and/or 605c) can be indicative (or include information indicative) of patient's location. In some instances, communications received from the patient system 502 can include indication(s) of a current location of the patient. In such instances, the communications 615 and 620 can be optional. In some instances, upon the medical management system 120 receiving a notification front a provider device (such as provider device 402a or 402b of a medical service (e.g., doctor visit, medical test(s), medical imaging service, etc.) provided to the patient, the patient location manager 215 can infer patient's current location from a location of the medical service provider. In response, the patient location manager 215 can initiate a process (e.g., series of communications) with a patient device (e.g., the medical dispensing device 302, a mobile device or other communication device) to confirm the inferred patient location or to determine a period of time associated with the inferred location. For example, the patient location manager 215 can cause a message to be sent to the patient requesting confirmation of the inferred location and/or how long the patient will be in the inferred location.

The patient location manager 215 can be configured to cause reporting of current patient location to provider devices (such as provider device 402 and/or 402b). For example, the patient location manager 215 can cause the medical manager 215 to send a message indicative of patient's current location to a doctor, pharmacy, other medical service provider or health care insurance provider associated with the patient.

The method 600 includes the medical management system 120 identifying a pharmacy for supplying medication to the patient (processing step 625). The identification of the pharmacy (processing step 625) can be based on one or more factors including a current location of the patient, a pharmacy inventory, a list of in-network and out of network pharmacies associated with a health insurance plan of the patient, patient preferences, medication prices associated with different pharmacies or a combination thereof.

The medical manager 220 or the prescription manager 222 can determine one or more pharmacy stores for supplying medication to the patient based on a current patient location. The medical management system 120 can maintain a default pharmacy store, for instance, associated with a permanent location of the patient, patient preferences and/or pharmacies affiliated with (or recognized as in-network provider by) a healthcare insurance provider of the patient. Upon determining that a current location of the patient is different (or far away) from the patient permanent location, the medical manager 220 and/or the prescription manager 222 can identify one or more pharmacy stores close (in distance) to the patient current location. The medical manager 220 and/or the prescription manager 222 can be configured to identify pharmacy store(s) satisfying user preferences and/or in-network criterion.

In some implementations, when the current patient location is determined to be different from the permanent location of the patient, the medical manager 220 and/or the prescription manager 222 can still select the default pharmacy store, a pharmacy store associated with patient permanent location or a pharmacy store far away from the current location of the patient. In such implementations, the medical manager 220 and/or the prescription manager 222 can instruct the selected pharmacy store to ship the medication to the current address of the patient. The medical management system 120 can provide options for the patient to select from, such as, (i) obtaining medication from a specific pharmacy store (e.g., a specific pharmacy store selected by the patient or the patient's healthcare insurance provider) or (ii) obtaining medication from the cheapest pharmacy store available, regardless of the patient location. The medical management system 120 can maintain payment information (such as credit card information, electronic wallet information or other payment information) associated with the patient for use to pay for medication to be supplied to the patient. In some implementations, the selected pharmacy store can provide electronic payment options directly to the patient or via the medical management system 120.

Referring back to FIG. 2 and Section B above, the medical management system 120 can also include an inventory manager 230 configured to remotely manage medication inventories for one or more pharmacy providers. The medical management system 120 can offer medication inventory management to pharmacy providers as a service. The medical management system 120 can offer one or more medical inventory management service options to providers. For example, a first service option can include full inventory management by the medical management system 120, in which case, tracking of medication (and/or medical devices) inventory is performed by the medical management system 120. The medical management system 120 can automatically generate inventory replenishment requests. Such requests can be approved by pharmacists (or other employees) associated with the pharmacy provider before being sent by the medical management system to medication and/or medical devices suppliers. Full inventory management by the medical management system 120 can result in reduced costs for pharmacy providers opting for such service option.

According to a second inventory management service option, pharmacy providers can opt to have the medical management system 120 remotely manage specific items (e.g., specific medication and/or specific medical devices). That is, the medical management system can partially manage the provider's inventory. In the case of full or partial inventory management, the medical management system 120 can be configured to manage medication (or medical devices) identification using RFID, barcodes or other identification means known in the art. For instance, the medical management system 120 can provide and/or track IDs for different medications, medical devices, or medication/medical devices provided to given patients.

In managing provider inventory, the medical management system 120 can be configured to receive periodic updates, such as from a point-of-sale (POS) terminal or other computer device associated with the provider, indicating amount of medication and/or medical devices sold since a previous update. The updates can be specific to given medication(s) or medical device(s) (e.g., in case of partial remote inventory management) or related to all medical products offered by the provider. The updates can be received on hourly basis, daily basis, weekly basis or according to other time frames. The medical management system 120 can also receive indications of amount of medication and/or medical devices provided by suppliers of the medical provider. The inventory manager 230 can use updates received from the medical provide to keep track of inventory status. That is, the inventory manager can subtract sold amounts of medication and/or medical devices from respective maintained amount parameters and add replenishment amounts provided by suppliers. The inventory manager 320 can use respective thresholds for different products to determine need for replenishment.

According to yet another service option, the medical management system 120 does not manage inventory for the provider. According to this option, pharmacy stores can report specific medication (and/or specific medical devices) inventory status to the medical system 120 either on a regular basis or based on request/response procedure(s).

The medical manager 220 and/or the prescription manager 222 can be configured to identify a pharmacy store for supplying medication to the patient (processing step 625) based on inventory statuses (with respect to the medication to be ordered) for different pharmacy stores. In cases where the medical management system 120 is fully or partially managing medical inventory for a given pharmacy provider, the medical manager 220 or the prescription manager 222 can request inventory status (with respect to the medication to be ordered for the patient) of a pharmacy store associated with the pharmacy provider from the inventory manager 230. For pharmacy providers not opting for remote inventory management, the medical management system can send requests to corresponding provider devices to check availability of the medication to be ordered. In some implementations, the medical manager 220 and/or the prescription manager can send such requests when no other providers opting for inventory management have the medication to be ordered or satisfy user and/or healthcare insurance requirements.

The medical manager 220 and/or the prescription manager 222 can be configured to send a request to the patient (e.g., via email, SMS, chat, phone call or other communication means) to approve a selected pharmacy store or to select a pharmacy store among a few identified stores. The medical management system 120 can select a final pharmacy store (and/or shipment option) based on patient response. The approval request to the patient can be optional.

Once a final pharmacy store is selected, the medical manager 220 and/or the prescription manager can send a medication supply/refill request to provider device (e.g., provider device 402*b*) associated with a selected provider or selected provider store (communication 630). The request 630 can include information indicative of in-store pick up or shipment of the medication, a shipment address, payment method or a combination thereof. In some implementations, the medical management system 120 can send the medication supply/refill request with indication of patient location to a pharmacy provider. The pharmacy provider can determine a respective pharmacy store based on the patient location.

The provider device 402*b* can send an acknowledgement back to the medical management system 120 (communication 635). The acknowledgement can include information indicative of a confirmation to supply the ordered medication, expected shipment or pickup time, a receipt (e.g., if payment is done electronically), or a combination thereof.

The medical management system 120 can forward the acknowledgement to the patient system 502 (communication 640). The communication 640 can be via email, SMS, chat, voice message, or other communication platform. The communication 640 can include a pick up time or date, pharmacy store address, transaction receipt or a combination thereof. In some implementations, the communication 640 is the last communication (or step) in the process of supplying the medication. In some implementations, the patient system 502 can send an acknowledgement back to the medical management system 120 confirming receipt of the communication 640.

Services provided by the medical management 120 can be offered under different service options or packages to medical service providers. Medical service providers can be allowed to select from a variety of offered service packages. For medical service providers, different service packages can include distinct combinations of services such as full or partial inventory management, access to GPS or location information, radio-frequency identification (RFID) for medication and/or medical devices, BLUETOOTH, Replenishment system for vapor store(s), advertisement options (e.g., ads to patients), access to statistical data generated by the medical management system 120, access to bidding options for providing medication (or medical devices) to patients, etc. The packages can range from a full service where the computer system of the medical provider is completely integrated within (or managed by) the medical management system 120 to a service where a provider device 402 of the medical provider is enabled to communicate with the medical management system for the purpose of medication supply/refill for patients. Through such communication, the medical care provider can access medicine related information of patients and provide instructions, which can administer treatment protocols to patients of the medical dispensing devices 302. In some implementations, the medical management system can provide the software to run on the medical dispensing devices 302 for download by patients of sellers of the medical dispensing devices 302. Distinct service packages can be associated with respective instances of mobile applications, computer applications and/or web applications. That is, depending on the selected service package, the medical service provider can download a respective instance of a computer application, mobile application and/or web application that allows consumption of the services associated with the selected service package. In some implementations, the medical management system 120 can provide a web platform to medical service providers. The services provided by (or data accessible through) the web platform to any given medical service provider depend on the selected service package by the medical service provider. The computer, mobile or web application/platform allows for communication between provider devices 402 with the medical management system 102.

In some implementations, the medical management system 120 can provide an electronic management platform for medical service providers. For example, the medical management system 120 can provide a full computerized management platform (e.g., web-based platform, computer application based platform, etc.) to a medical service provider (such as a hospital, a pharmacy provider, a medical lab, a doctor office, a medical imaging facility). In such implementations, the medical service provider system is fully integrated within (and/or managed by) the medical management system 120.

In some implementations, the medical managements system 120 can provide a variety of service packages for patients. Distinct service packages can include different combinations of services offered by the medical management system 120 such as medical record management, medical services (such as doctor appointments, appointments for medical tests and/or medical imaging services, etc.), location management, electronic payment options, price bargaining options, etc. The medical management system 120 can provide multiple mobile, computer and/or web application/platform instances associated with respective offered service packages. A patient can download an application instance onto a respective medical dispensing device 302, mobile device or other communication device. Access to a web platform/application offered by the medical management system 120 can involve a form of user authentication (e.g., login and password, fingerprint authentication or other type of biometric authentication).

While the invention has been particularly shown and described with reference to specific embodiments, it should be understood by those skilled in the art that various changes in form and detail may be made therein without departing from the spirit and scope of the invention described in this disclosure.

While this specification contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

What is claimed is:

1. A remote medical management system, comprising:
one or more processors, coupled to memory, the one or more processors intermediary via one or more networks to a plurality of medical dispensing devices and a plurality of provider devices;
a first communication device, coupled to the one or more processors, and configured to communicate with the plurality of medical dispensing devices configured to dispense medication to patients, each medical dispensing device of the plurality of medical dispensing devices comprising one or more sensors for sensing a medication level of one or more cartridges of each medical dispensing device, an outlet through which medication is dispensed from the medical dispensing device and one or more actuators to dispense medicine from the one or more cartridges through the outlet;
a second communication device coupled to the one or more processors, and configured to communicate with the plurality of provider devices through which medical care providers can provide information regarding services provided to patients or instructions associated with medication use;
wherein the one or more processors are configured to:
communicate with the plurality of medical dispensing devices via the first communication device and the plurality of provider devices via the second communication device;
receive GPS data communicated by the plurality of medical dispensing devices to the manager;
detect medication supply events based on information about the medication level of one or more cartridges of the plurality of medical dispensing devices communicated by the medical dispensing devices over the one or more networks and received via the first communication device;
receive via the second communication device; over the one or more networks dosage instructions from the plurality of provider devices for medication in the one or more cartridges of the plurality of medical dispensing devices;
determine a refill event for a medical dispensing device of the plurality of medical dispensing devices based at least on the medication level of the one or more cartridges of the medical dispensing device and a dosage instruction received from one of the plurality of provider devices for the patient of the medical dispensing devices;
determine based on the GPS data of the medical dispensing device a location of the patient of the medical dispensing device and automatically execute a refill process of medication for the patient based on the location of the patient; and send instructions to the medical dispensing device to cause one or more actuators of the medical dispensing device to dispense medicine from the one or more cartridges.

2. The remote medical management system of claim 1, wherein the medication level includes a level of consumed medication of a level of medication remaining in the one or more cartridges.

3. The remote medical management system of claim 1, wherein the one or more processors are further configured to determine a provider facility for providing the medication to the patient based on the location of the patient.

4. The remote medical management system of claim 3, wherein the one or more processors are further configured to automatically send an order to the provider facility for the medication.

5. The remote medical management system of claim 1, wherein the one or more processors are further configured to send instructions to the medical dispensing device to specify a length of time for which to keep one or more valves open to dispense the dosage.

6. The remote medical management system of claim 1, wherein the one or more processors are further configured to send instructions to the medical dispensing device to regulate temperature around the one or more cartridges within which the medication is stored.

7. The remote medical management system of claim 1, wherein the one or more processors are further configured to monitor via the GPS data a location of the medical dispensing device.

8. The remote medical management system of claim 7, further comprising one or more location based policies, the one or more location based policies to allow the medical dispensing device to only dispense at predetermined locations.

9. The remote medical management system of claim 1, wherein the one or more processors are further configured to apply a location determination policy to determine a location of interest associated with the patient of the medical dispensing device.

10. The remote medical management system of claim 9, wherein the location determination policy includes one or more rules, the one or more rules including one or more of the following: a threshold for a period of stay by the patient at a detected location, a frequency of visiting the detected location and a distance from an addressed associated with the patient.

11. The remote medical management system of claim 10, wherein the one or more processors are further configured to determined based on recorded patient location data and the location determination policy that the patient is more often in a first location during a first period of the year and in a second location during a second period of the year.

12. The remote medical management system of claim 9, the one or more processors are further configured to communicate via the second communication device over the one or more networks to one or more provided devices the location of the patient.

13. The remote medical management system of claim 1, further comprising one or more communications devices through which a provider of a provider device of the plurality of provider devices remotely administers medications via the medical dispensing device.

14. The remote medical management system of claim 13, wherein the provider via the provider device adjusts the dosage of the medication on the medical dispensing device.

15. The remote medical management system of claim 13, wherein the provider via the provider device adjusts a time at which the medication on the medical dispensing device is dispensed.

16. The remote medical management system of claim 1, wherein the one or more processors are further configured to receive from the plurality of medical dispensing devices via the first communication device reports about dispensing events.

17. The remote medical management system of claim 16, wherein the one or more processors are further configured to determine a dispensing rate of the medication based at least on the dispensing events.

18. The remote medical management system of claim 17, wherein the one or more processors are further configured to determine an expected refill date for which to execute the refill process.

19. The remote medical management system of claim 1, wherein the medical dispensing device is a programmable, remotely controlled prescription device.

20. The remote medical management system of claim 1, wherein the medical dispensing device is configured to communicate with a computing device of the patient to verify an identify of the patient accessing the medical dispensing device.

* * * * *